US008389260B2

(12) United States Patent
DiCosimo et al.

(10) Patent No.: US 8,389,260 B2
(45) Date of Patent: Mar. 5, 2013

(54) PERHYDROLASE VARIANT PROVIDING IMPROVED SPECIFIC ACTIVITY

(75) Inventors: Robert DiCosimo, Chadds Ford, PA (US); Mark Scott Payne, Wilmington, DE (US); John Edward Gavagan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/328,418

(22) Filed: Dec. 16, 2011

(65) Prior Publication Data

US 2012/0156162 A1 Jun. 21, 2012

Related U.S. Application Data

(60) Provisional application No. 61/425,561, filed on Dec. 21, 2010, provisional application No. 61/434,725, filed on Jan. 20, 2011.

(51) Int. Cl.
*C12N 9/18* (2006.01)
*C12P 7/40* (2006.01)
*A61L 9/00* (2006.01)

(52) U.S. Cl. ........................ 435/197; 435/136; 424/76.1

(58) Field of Classification Search ........................ None
See application file for complete search history.

(56) References Cited

U.S. PATENT DOCUMENTS 3,974,082 A 8/1976 Weyn
4,585,150 A 4/1986 Beacham et al.
5,116,575 A 5/1992 Badertscher et al.
5,296,161 A 3/1994 Wiersema et al.
5,338,676 A 8/1994 Mitsushima et al.
5,364,554 A 11/1994 Stanislowski et al.
5,398,846 A 3/1995 Corba et al.
5,528,152 A 6/1996 Hinoshita et al.
5,552,018 A 9/1996 Devenyns
5,624,634 A 4/1997 Brougham et al.
5,683,724 A 11/1997 Hei et al.
5,932,532 A 8/1999 Ghosh et al.
6,183,807 B1 2/2001 Gutzmann et al.
6,210,639 B1 4/2001 Vlass et al.
6,319,888 B2 11/2001 Wei et al.
6,391,840 B1 5/2002 Thompson et al.
6,518,307 B2 2/2003 McKenzie et al.
6,545,047 B2 4/2003 Gutzmann et al.
7,550,420 B2 6/2009 DiCosimo et al.
7,723,083 B2 5/2010 DiCosimo et al.
7,807,425 B2 10/2010 DiCosimo et al.
7,910,347 B1 3/2011 DiCosimo et al.
7,923,233 B1 4/2011 DiCosimo et al.
7,927,854 B1 4/2011 DiCosimo et al.
7,932,072 B1 4/2011 DiCosimo et al.
7,951,566 B2 5/2011 DiCosimo et al.
7,960,528 B1 6/2011 DiCosimo et al.
7,964,378 B2 6/2011 DiCosimo et al.
8,062,875 B2 11/2011 DiCosimo et al.
2003/0026846 A1 2/2003 Hei et al.
2005/0008526 A1 1/2005 Bianchetti et al.
2008/0176299 A1 7/2008 DiCosimo et al.
2010/0041752 A1 2/2010 DiCosimo et al.
2010/0086510 A1 4/2010 DiCosimo et al.
2010/0086621 A1 4/2010 DiCosimo et al.
2010/0087528 A1 4/2010 DiCosimo et al.
2010/0087529 A1 4/2010 DiCosimo et al.
2010/0168235 A1 7/2010 DiCosimo et al.
2011/0136907 A1 6/2011 DiCosimo et al.
2011/0236336 A1 9/2011 DiCosimo et al.
2011/0236338 A1 9/2011 DiCosimo et al.
2011/0236339 A1 9/2011 DiCosimo et al.
2011/0244535 A1 10/2011 DiCosimo et al.

FOREIGN PATENT DOCUMENTS

EP 1040222 B1 10/2000
EP 0807156 B1 3/2001
WO WO 99/32710 7/1999
WO WO 00/61713 A1 3/2000
WO WO 2007/070609 6/2007

OTHER PUBLICATIONS

Gabrielson, et al., Evaluation of Redox Indicators and the Use of Digital Scanners and Spectrophotometer . . . , J: Microbiol. Methods, vol. 50:63-73, 2002.
Gilbert et al., Recent Advances in Carbohydrate Bioengineering, The Royal Society of Chemistry, Cambridge, pp. 3-12, 1999.
Mitsushima et al Gene Cloning, Nucleotide Sequence, and Expression.., Appl. Env. Microbiol. 61(6):2224-2229, 1995.
Vincent et al., Multifunctional Xylooligosaccharide/Cephalosporin C Deacetylase . . . , J. Mol. Biol., 330:593-606, 2003.
Co-pending U.S. Appl. No. 13/328,305, filed Dec. 16, 2011.
Co-pending U.S. Appl. No. 13/328,327, filed Dec. 16, 2011.
Co-pending U.S. Appl. No. 13/328,336, filed Dec. 16, 2011.
Co-pending U.S. Appl. No. 13/328,350, filed Dec. 16, 2011.
Co-pending U.S. Appl. No. 13/328,364, filed Dec. 16, 2011.
Co-pending U.S. Appl. No. 13/328,381, filed Dec. 16, 2011.
Co-pending U.S. Appl. No. 13/328,390, filed Dec. 16, 2011.

*Primary Examiner* — Tekchand Saidha
*Assistant Examiner* — Md. Younus Meah

(57) ABSTRACT

An acetyl xylan esterase variant having perhydrolytic activity is provided for producing peroxycarboxylic acids from carboxylic acid esters and a source of peroxygen. More specifically, a *Thermotoga maritime* acetyl xylan esterase gene was modified using error-prone PCR and site-directed mutagenesis to create an enzyme catalyst characterized by an increase in specific activity. The variant acetyl xylan esterase may be used to produce peroxycarboxylic acids suitable for use in a variety of applications such as cleaning, disinfecting, sanitizing, bleaching, wood pulp processing, and paper pulp processing applications.

17 Claims, No Drawings

PERHYDROLASE VARIANT PROVIDING IMPROVED SPECIFIC ACTIVITY

CROSS-REFERENCE TO RELATED APPLICATIONS

This application claims benefit of U.S. Provisional Patent Application No. 61/425,561, filed Dec. 21, 2010, and U.S. Provisional Patent Application No. 61/434,725, filed Jan. 20, 2011, each of which is incorporated by reference herein in its entirety.

TECHNICAL FIELD

The invention relates to the field of peroxycarboxylic acid biosynthesis and enzyme catalysis. More specifically, an enzyme catalyst comprising a variant enzyme having perhydrolytic activity is provided having an increase in specific activity. Methods of using the present enzyme catalyst to produce peroxycarboxylic acids are also provided.

BACKGROUND

Peroxycarboxylic acid compositions can be effective antimicrobial agents. Methods of using peroxycarboxylic acids to clean, disinfect, and/or sanitize hard surfaces, textiles, meat products, living plant tissues, and medical devices against undesirable microbial growth have been described (U.S. Pat. Nos. 6,545,047; 6,183,807; 6,518,307; U.S. Patent Application Publication No. 2003-0026846; and U.S. Pat. No. 5,683,724). Peroxycarboxylic acids have also been used in a various bleaching applications including, but not limited to, wood pulp bleaching/delignification and laundry care applications (European Patent 1040222B1; U.S. Pat. Nos. 5,552,018; 3,974,082; 5,296,161; and 5,364,554). The desired efficacious concentration of peroxycarboxylic acid may vary according to the product application (for example, ca. 500 ppm to 1000 ppm for medical instrument disinfection, ca. 30 ppm to 80 ppm for laundry bleaching or disinfection applications) in 1 min to 5 min reaction time at neutral pH.

Enzymes structurally classified as members of family 7 of the carbohydrate esterases (CE-7) have been employed as perhydrolases to catalyze the reaction of hydrogen peroxide (or alternative peroxide reagent) with alkyl esters of carboxylic acids in water at a basic to acidic pH range (from ca. pH 10 to ca. pH 5) to produce an efficacious concentration of a peroxycarboxylic acid for such applications as disinfection (such as medical instruments, hard surfaces, textiles), bleaching (such as wood pulp or paper pulp processing/delignification, textile bleaching and laundry care applications), and other laundry care applications such as destaining, deodorizing, and sanitization (U.S. Pat. Nos. 7,964,378; 7,951,566; and 7,723,083 and Published U.S. Patent Application Nos. 2008-0176299, and 2010-0041752 to DiCosimo et al.). The CE-7 enzymes have been found to have high specific activity for perhydrolysis of esters, particularly acetyl esters of alcohols, diols and glycerols.

Published U.S. Patent Application No. 2010-0087529 to DiCosimo et al. describes several variant CE-7 perhydrolases derived from several *Thermotoga* sp. having higher perhydrolytic specific activity and/or improved selectivity for perhydrolysis when used to prepare peroxycarboxylic acid from carboxylic acid esters. Two of the variants described in Published U.S. Patent Application No. 2010-0087529, *Thermotoga maritime* C277S and *Thermotoga maritima* C277T, exhibited a significant improvement in specific activity relative to the *T. maritima* wild-type enzyme.

*Thermotoga maritima* variants having higher peracid stability were also reported by DiCosimo et al. in U.S. Pat. Nos. 7,927,854; 7,923,233; 7,932,072; and 7,910,347, and U.S. patent application Ser. No. 12/632,462. Each variant was characterized as having an increased peracetic acid formation to peracetic acid hydrolysis ratio (PAAF:PAAH) when compared to the *T. maritima* wild-type perhydrolase or the *T. maritima* C277S variant perhydrolase.

Several variants of the *Thermotoga maritima* C2775 perhydrolase have been identified which have higher specific activity for the perhydrolysis of esters when compared to the specific activity of the *Thermotoga maritima* C277S (U.S. patent application Ser. Nos. 13/070,123; 13/070,130; 13/070,135; 13/070,144; and 13/070,149 to DiCosimo et al.). However, there remains a need to identify additional variants having an increase in perhydrolytic specific activity.

The problem to be solved is to provide an enzyme catalyst comprising a CE-7 perhydrolase having higher specific activity for the perhydrolysis of esters when compared to the specific activity of the *Thermotoga maritima* C277S perhydrolase or the *Thermotoga maritima* C277T perhydrolase.

SUMMARY

Nucleic acid molecules encoding the *Thermotoga maritima* acetyl xylan esterase variants C277S or C277T were mutated to create libraries of variant enzymes having perhydrolytic activity. Several perhydrolase variants were identified having an increase in specific activity when compared to the parent enzyme from which they were derived (i.e., the *Thermotoga maritima* C277S perhydrolase or the *Thermotoga maritima* C277T perhydrolase) under the same assay conditions.

In one embodiment, an isolated nucleic acid molecule encoding a polypeptide having perhydrolytic activity is provided selected from the group consisting of:

(a) a polynucleotide encoding a polypeptide having perhydrolytic activity, said polypeptide comprising the amino acid sequence of SEQ ID NO: 30;

(b) a polynucleotide comprising the nucleic acid sequence of SEQ ID NO: 29; and (c) a polynucleotide fully complementary to the polynucleotide of (a) or (b).

In other embodiments, a vector, a recombinant DNA construct, and a recombinant host cell comprising the present polynucleotide are also provided.

In another embodiment, a method for transforming a cell is provided comprising transforming a cell with the above nucleic acid molecule.

In another embodiment, an isolated polypeptide having perhydrolysis activity is provided comprising the amino acid sequence of SEQ ID NO: 30.

In one embodiment, the variant polypeptide having perhydrolytic activity is characterized by an increase in specific activity (as determined by an increased amount of peroxycarboxylic acid produced) when compared to the specific activity of the *Thermotoga maritime* C277S variant or the *Thermotoga maritime* C277T variant (Published U.S. Patent Application No. 2010-0087529 to DiCosimo et al) under identical reaction conditions.

In another embodiment, a process for producing a peroxycarboxylic acid is also provided comprising:

(a) providing a set of reaction components comprising:

(1) at least one substrate selected from the group consisting of:

(i) one or more esters having the structure $$[X]_m R_5$$

wherein

X=an ester group of the formula $R_6$—C(O)O;

$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester or carboxylic acid group; wherein $R_5$ optionally comprises one or more ether linkages;

m=is an integer ranging from 1 to the number of carbon atoms in $R_5$; and wherein said esters have solubility in water of at least 5 ppm at 25° C.;

(ii) one or more glycerides having the structure

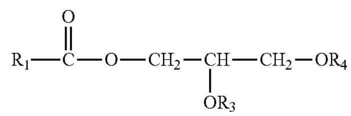

wherein $R_1$=C1 to C21 straight chain or branched chain alkyl optionally substituted with an hydroxyl or a C1 to C4 alkoxy group and $R_3$ and $R_4$ are individually H or $R_1$C(O);

(iii) one or more esters of the formula:

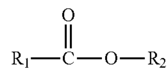

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10;

(iv) one or more acylated monosaccharides, acylated disaccharides, or acylated polysaccharides; and (v) any combination of (i) through (iv);

(2) a source of peroxygen; and (3) an enzyme catalyst comprising a polypeptide having perhydrolytic activity, said polypeptide comprising the amino acid sequence of SEQ ID NO: 30;

(b) combining the set of reaction components under suitable reaction conditions whereby peroxycarboxylic acid is produced; and (c) optionally diluting the peroxycarboxylic acid produced in step (b).

In another embodiment, a process is provided further comprising a step (d) wherein the peroxycarboxylic acid produced in step (b) or step (c) is contacted with a hard surface, an article of clothing or an inanimate object whereby the hard surface, article of clothing or inanimate object is disinfected, sanitized, bleached, destained, deodorized or any combination thereof.

In another embodiment, a composition is provided comprising:

(a) a set of reaction components comprising:

(1) at least one substrate selected from the group consisting of:

(i) one or more esters having the structure $[X]_mR_5$ wherein

X=an ester group of the formula $R_6$—C(O)O;

$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m=is an integer ranging from 1 to the number of carbon atoms in $R_5$; and wherein said esters have solubility in water of at least 5 ppm at 25° C.;

(ii) one or more glycerides having the structure

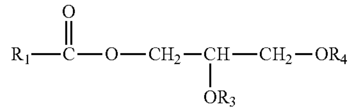

wherein $R_1$=C1 to C21 straight chain or branched chain alkyl optionally substituted with an hydroxyl or a C1 to C4 alkoxy group and $R_3$ and $R_4$ are individually H or $R_1$C(O);

(iii) one or more esters of the formula:

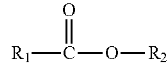

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10;

(iv) one or more acylated monosaccharides, acylated disaccharides, or acylated polysaccharides; and (v) any combination of (i) through (iv);

(2) a source of peroxygen; and (3) an enzyme catalyst comprising a polypeptide, said polypeptide comprising perhydrolytic activity having the amino acid sequence of SEQ ID NO: 30; and (b) at least one peroxycarboxylic acid formed upon combining the set of reaction components of (a).

The present process produces the desired peroxycarboxylic acid upon combining the reaction components. The reaction components may remain separated until use.

In a further aspect, a peroxycarboxylic acid generation and delivery system is provided comprising:

(a) a first compartment comprising (1) an enzyme catalyst comprising a polypeptide having perhydrolytic activity, said polypeptide comprising the amino acid sequence of SEQ ID NO: 30;

(2) at least one substrate selected from the group consisting of:

(i) one or more esters having the structure $[X]_m R_5$ wherein

X=an ester group of the formula $R_6$—C(O)O;

$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m=is an integer ranging from 1 to the number of carbon atoms in $R_5$; and wherein said esters have solubility in water of at least 5 ppm at 25° C.;

(ii) one or more glycerides having the structure

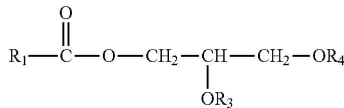

wherein $R_1$=C1 to C21 straight chain or branched chain alkyl optionally substituted with an hydroxyl or a C1 to C4 alkoxy group and $R_3$ and $R_4$ are individually H or $R_1$C(O);

(iii) one or more esters of the formula:

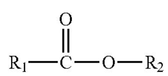

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10;

(iv) one or more acylated monosaccharides, acylated disaccharides, or acylated polysaccharides; and (v) any combination of (i) through (iv); and (3) an optional buffer; and (b) a second compartment comprising (1) source of peroxygen;

(2) a peroxide stabilizer; and (3) an optional buffer.

In a further embodiment, a laundry care composition is provided comprising a polypeptide comprising the amino acid sequence of SEQ ID NO: 30.

In a further embodiment, a personal care composition is provided comprising a polypeptide comprising the amino acid sequence of SEQ ID NO: 30.

BRIEF DESCRIPTION OF THE BIOLOGICAL SEQUENCES

The following sequences comply with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO: 1 is the nucleic acid sequence of the codon-optimized coding region encoding the wild-type *Thermotoga maritima* acetyl xylan esterase having perhydrolytic activity.

SEQ ID NO: 2 is the amino acid sequence of the wild-type *Thermotoga maritima* acetyl xylan esterase having perhydrolytic activity.

SEQ ID NOs: 3 and 4 are the nucleic acid sequences of primers used to prepare the C277T variant acetyl xylan esterase.

SEQ ID NO: 5 is the amino acid sequence of the C277T variant acetyl xylan esterase having perhydrolytic activity (Published U.S. Patent Application No. 2010-0087529 to DiCosimo et al.).

SEQ ID NO: 6 is the nucleic acid sequence of the plasmid pSW202/C277T.

SEQ ID NOs: 7 and 8 are the nucleic acid sequences of primers used for error-prone PCR.

SEQ ID NO: 9 is the nucleic acid sequence encoding the variant acetyl xylan esterase 006D11 having the following substitutions relative to the wild-type *Thermotoga maritima* acetyl xylan esterase amino acid sequence: W28R/P84S/S201G/E243D/C277T.

SEQ ID NO: 10 is the amino acid sequence of the 006D11 variant acetyl xylan esterase.

SEQ ID NO: 11 is the nucleic acid sequence encoding the variant acetyl xylan esterase 006F12 having the following substitutions relative to the wild-type *Thermotoga maritima* acetyl xylan esterase amino acid sequence: R261S/I264F/C277T.

SEQ ID NO: 12 is the amino acid sequence of the 006F12 variant acetyl xylan esterase.

SEQ ID NO: 13 is the nucleic acid sequence encoding the variant acetyl xylan esterase 006D10 having the following substitutions relative to the wild-type *Thermotoga maritima* acetyl xylan esterase amino acid sequence: W28C/L32P/D151E/C277T.

SEQ ID NO: 14 is the amino acid sequence of the 006D10 variant acetyl xylan esterase.

SEQ ID NO: 15 is the nucleic acid sequence encoding the variant acetyl xylan esterase 006B12 having the following substitutions relative to the wild-type *Thermotoga maritima* acetyl xylan esterase amino acid sequence: W28C/F104S/C277T.

SEQ ID NO: 16 is the amino acid sequence of the 006B12 variant acetyl xylan esterase.

SEQ ID NO: 17 is the nucleic acid sequence encoding the variant acetyl xylan esterase 006E11 having the following substitutions relative to the wild-type *Thermotoga maritima* acetyl xylan esterase amino acid sequence: V183D/C277T.

SEQ ID NO: 18 is the amino acid sequence of the 006E11 variant acetyl xylan esterase.

SEQ ID NO: 19 is the nucleic acid sequence encoding the variant acetyl xylan esterase 006H5 having the following substitutions relative to the wild-type *Thermotoga maritima* acetyl xylan esterase amino acid sequence: C277T/L318P.

SEQ ID NO: 20 is the amino acid sequence of the 006H5 variant acetyl xylan esterase.

SEQ ID NO: 21 is the nucleic acid sequence encoding the variant acetyl xylan esterase 006B5 having the following substitutions relative to the wild-type *Thermotoga maritima* acetyl xylan esterase amino acid sequence: P265L/C277T/I297N.

SEQ ID NO: 22 is the amino acid sequence of the 006B5 variant acetyl xylan esterase.

SEQ ID NO: 23 is the nucleic acid sequence encoding the variant acetyl xylan esterase 006F3 having the following substitutions relative to the wild-type *Thermotoga maritima* acetyl xylan esterase amino acid sequence: P16L/F38S/T53N/R159C/V183D/C277T.

SEQ ID NO: 24 is the amino acid sequence of the 006F3 variant acetyl xylan esterase.

SEQ ID NO: 25 is the nucleic acid sequence encoding the variant acetyl xylan esterase 006G10 having the following substitutions relative to the wild-type *Thermotoga maritima* acetyl xylan esterase amino acid sequence: R15H/Q176H/L208Q/C277T.

SEQ ID NO: 26 is the amino acid sequence of the 006G10 variant acetyl xylan esterase.

SEQ ID NO: 27 is the nucleic acid sequence encoding the variant acetyl xylan esterase 006F1 having the following substitutions relative to the wild-type *Thermotoga maritima* acetyl xylan esterase amino acid sequence: L32P/C277T.

SEQ ID NO: 28 is the amino acid sequence of the 006F1 variant acetyl xylan esterase.

SEQ ID NO: 29 is the nucleic acid sequence encoding the variant acetyl xylan esterase 006A10 having the following substitutions relative to the wild-type *Thermotoga maritima* acetyl xylan esterase amino acid sequence: F268S/C277T.

SEQ ID NO: 30 is the amino acid sequence of the 006A10 variant acetyl xylan esterase.

SEQ ID NO: 31 is the nucleic acid sequence encoding the variant acetyl xylan esterase 006G6 having the following substitutions relative to the wild-type *Thermotoga maritima* acetyl xylan esterase amino acid sequence: E29G/S62P/F174L/C277T.

SEQ ID NO: 32 is the amino acid sequence of the 006G6 variant acetyl xylan esterase.

SEQ ID NO: 33 is the nucleic acid sequence encoding the variant acetyl xylan esterase 006E10 having the following substitutions relative to the wild-type *Thermotoga maritima* acetyl xylan esterase amino acid sequence: R218C/C277T/F317L.

SEQ ID NO: 34 is the amino acid sequence of the 006E10 variant acetyl xylan esterase.

SEQ ID NO: 35 is the nucleic acid sequence encoding the variant acetyl xylan esterase 006D9 having the following substitutions relative to the wild-type *Thermotoga maritime* acetyl xylan esterase amino acid sequence: C277T/R296P.

SEQ ID NO: 36 is the amino acid sequence of the 006D9 variant acetyl xylan esterase.

SEQ ID NO: 37 is the nucleic acid sequence encoding the variant acetyl xylan esterase 006F7 having the following substitutions relative to the wild-type *Thermotoga maritime* acetyl xylan esterase amino acid sequence: E9K/G255C/C277T.

SEQ ID NO: 38 is the amino acid sequence of the 006F7 variant acetyl xylan esterase.

SEQ ID NO: 39 is the nucleic acid sequence encoding the variant acetyl xylan esterase 006E12 having the following substitutions relative to the wild-type *Thermotoga maritime* acetyl xylan esterase amino acid sequence: H227L/T233A/C277T/A290V.

SEQ ID NO: 40 is the amino acid sequence of the 006E12 variant'acetyl xylan esterase.

SEQ ID NO: 41 is the nucleic acid sequence encoding the variant acetyl xylan esterase 006F8 having the following substitutions relative to the wild-type *Thermotoga maritime* acetyl xylan esterase amino acid sequence: Q67R/K82E/C277T.

SEQ ID NO: 42 is the amino acid sequence of the 006F8 variant acetyl xylan esterase.

SEQ ID NO: 43 is the nucleic acid sequence encoding the variant acetyl xylan esterase 006G8 having the following substitutions relative to the wild-type *Thermotoga maritima* acetyl xylan esterase amino acid sequence: F247L/C277T/V282D.

SEQ ID NO: 44 is the amino acid sequence of the 006G8 variant acetyl xylan esterase.

SEQ ID NO: 45 is the nucleic acid sequence encoding the variant acetyl xylan esterase 006G11 having the following substitutions relative to the wild-type *Thermotoga maritima* acetyl xylan esterase amino acid sequence: D254G/C277T.

SEQ ID NO: 46 is the amino acid sequence of the 006G11 variant acetyl xylan esterase.

SEQ ID NO: 47 is the nucleic acid sequence encoding the variant acetyl xylan esterase 006E9 having the following substitutions relative to the wild-type *Thermotoga maritima* acetyl xylan esterase amino acid sequence: E17V/R261H/C277T.

SEQ ID NO: 48 is the amino acid sequence of the 006E9 variant acetyl xylan esterase.

SEQ ID NO: 49 is the nucleic acid sequence encoding the variant acetyl xylan esterase 006F10 having the following substitutions relative to the wild-type *Thermotoga maritima* acetyl xylan esterase amino acid sequence: F24L/T31S/E48V/C277T/K316E.

SEQ ID NO: 50 is the amino acid sequence of the 006F10 variant acetyl xylan esterase.

SEQ ID NO: 51 is the nucleic acid sequence encoding the variant acetyl xylan esterase 006F5 having the following substitutions relative to the wild-type *Thermotoga maritima* acetyl xylan esterase amino acid sequence: V43G/G63C/H100L/C277T/A284V.

SEQ ID NO: 52 is the amino acid sequence of the 006F5 variant acetyl xylan esterase.

SEQ ID NO: 53 is the nucleic acid sequence encoding the variant acetyl xylan esterase 006E7 having the following substitutions relative to the wild-type *Thermotoga maritima* acetyl xylan esterase amino acid sequence: F258Y/C277T/E294G/L318P.

SEQ ID NO: 54 is the amino acid sequence of the 006E7 variant acetyl xylan esterase.

SEQ ID NO: 55 is the nucleic acid sequence encoding the variant acetyl xylan esterase 006G12 having the following substitutions relative to the wild-type *Thermotoga maritima* acetyl xylan esterase amino acid sequence: F161L/C277T.

SEQ ID NO: 56 is the amino acid sequence of the 006G12 variant acetyl xylan esterase.

SEQ ID NO: 57 is the nucleic acid sequence encoding the variant acetyl xylan esterase 006H01 having the following substitutions relative to the wild-type *Thermotoga maritima* acetyl xylan esterase amino acid sequence: F253S/C277T.

SEQ ID NO: 58 is the amino acid sequence of the 006H01 variant acetyl xylan esterase.

SEQ ID NO: 59 is the nucleic acid sequence encoding the variant acetyl xylan esterase 006G2 having the following substitutions relative to the wild-type *Thermotoga maritima* acetyl xylan esterase amino acid sequence: F24I/C277T.

SEQ ID NO: 60 is the amino acid sequence of the 006G2 variant acetyl xylan esterase.

SEQ ID NO: 61 is the nucleic acid sequence encoding the variant acetyl xylan esterase 006F6 having the following substitutions relative to the wild-type *Thermotoga maritima* acetyl xylan esterase amino acid sequence: A206T/C277T.

SEQ ID NO: 62 is the amino acid sequence of the 006F6 variant acetyl xylan esterase.

SEQ ID NO: 63 is the nucleic acid sequence encoding the variant acetyl xylan esterase 006C10 having the following substitutions relative to the wild-type *Thermotoga maritima* acetyl xylan esterase amino acid sequence: E55K/C277T.

SEQ ID NO: 64 is the amino acid sequence of the 006C10 variant acetyl xylan esterase.

SEQ ID NO: 65 is the nucleic acid sequence encoding the variant acetyl xylan esterase 006F9 having the following substitutions relative to the wild-type *Thermotoga maritima* acetyl xylan esterase amino acid sequence: Q67R/C277T.

SEQ ID NO: 66 is the amino acid sequence of the 006F9 variant acetyl xylan esterase.

SEQ ID NOs: 67 and 68 are the nucleic acid sequences of primers used to prepare the C277S variant acetyl xylan esterase.

SEQ ID NO: 69 is the amino acid sequence of the C277S variant acetyl xylan esterase having perhydrolytic activity (U.S. patent application Ser. No. 12/572,094 to DiCosimo et al.).

SEQ ID NO: 70 is the nucleic acid sequence of the plasmid pSW202/C277S.

SEQ ID NOs: 71-82 are primers.

SEQ ID NO: 83 is the nucleic acid sequence encoding the variant acetyl xylan esterase 873C8 having the following substitutions relative to the wild-type *Thermotoga maritima* acetyl xylan esterase amino acid sequence: S35R/C277S.

SEQ ID NO: 84 is the amino acid sequence of the 873C8 variant acetyl xylan esterase.

SEQ ID NO: 85 is the nucleic acid sequence encoding the variant acetyl xylan esterase 873D7 having the following substitutions relative to the wild-type *Thermotoga maritima* acetyl xylan esterase amino acid sequence: S35K/C277S.

SEQ ID NO: 86 is the amino acid sequence of the 873D7 variant acetyl xylan esterase.

SEQ ID NO: 87 is the nucleic acid sequence encoding the variant acetyl xylan esterase 873D3 having the following substitutions relative to the wild-type *Thermotoga maritima* acetyl xylan esterase amino acid sequence: S35E/C277S.

SEQ ID NO: 88 is the amino acid sequence of the 873D3 variant acetyl xylan esterase.

SEQ ID NO: 89 is the nucleic acid sequence encoding the variant acetyl xylan esterase 873C9 having the following substitutions relative to the wild-type *Thermotoga maritima* acetyl xylan esterase amino acid sequence: S35N/C277S.

SEQ ID NO: 90 is the amino acid sequence of the 873C9 variant acetyl xylan esterase.

SEQ ID NO: 91 is the nucleic acid sequence encoding the variant acetyl xylan esterase 873H5 having the following substitutions relative to the wild-type *Thermotoga maritima* acetyl xylan esterase amino acid sequence: K77A/C277S.

SEQ ID NO: 92 is the amino acid sequence of the 873H5 variant acetyl xylan esterase.

SEQ ID NO: 93 is the nucleic acid sequence encoding the variant acetyl xylan esterase 873G12 having the following substitutions relative to the wild-type *Thermotoga maritime* acetyl xylan esterase amino acid sequence: K77V/C277S.

SEQ ID NO: 94 is the amino acid sequence of the 873G12 variant acetyl xylan esterase.

SEQ ID NO: 95 is the nucleic acid sequence encoding the variant acetyl xylan esterase 873H1 having the following substitutions relative to the wild-type *Thermotoga maritime* acetyl xylan esterase amino acid sequence: K77D/C277S.

SEQ ID NO: 96 is the amino acid sequence of the 873H1 variant acetyl xylan esterase.

SEQ ID NO: 97 is the nucleic acid sequence encoding the variant acetyl xylan esterase 873A4 having the following substitutions relative to the wild-type *Thermotoga maritime* acetyl xylan esterase amino acid sequence: L125M/C277S.

SEQ ID NO: 98 is the amino acid sequence of the 873A4 variant acetyl xylan esterase.

SEQ ID NO: 99 is the nucleic acid sequence encoding the variant acetyl xylan esterase 873A9 having the following substitutions relative to the wild-type *Thermotoga maritima* acetyl xylan esterase amino acid sequence: L125R/C277S.

SEQ ID NO: 100 is the amino acid sequence of the 873A9 variant acetyl xylan esterase.

SEQ ID NO: 101 is the nucleic acid sequence encoding the variant acetyl xylan esterase 873B4 having the following substitutions relative to the wild-type *Thermotoga maritima* acetyl xylan esterase amino acid sequence: A266P/C277S.

SEQ ID NO: 102 is the amino acid sequence of the 873B4 variant acetyl xylan esterase.

SEQ ID NO: 103 is the nucleic acid sequence encoding the variant acetyl xylan esterase 873B2 having the following substitutions relative to the wild-type *Thermotoga maritime* acetyl xylan esterase amino acid sequence: A266D/C277S.

SEQ ID NO: 104 is the amino acid sequence of the 873B2 variant acetyl xylan esterase.

SEQ ID NO: 105 is the nucleic acid sequence encoding the variant acetyl xylan esterase 873G7 having the following substitutions relative to the wild-type *Thermotoga maritime* acetyl xylan esterase amino acid sequence: A2661/C277S.

SEQ ID NO: 106 is the amino acid sequence of the 873G7 variant acetyl xylan esterase.

SEQ ID NO: 107 is the nucleic acid sequence encoding the variant acetyl xylan esterase 873C3 having the following substitutions relative to the wild-type *Thermotoga maritime* acetyl xylan esterase amino acid sequence: A266E/C277S.

SEQ ID NO: 108 is the amino acid sequence of the 873C3 variant acetyl xylan esterase.

SEQ ID NO: 109 is the nucleic acid sequence encoding the variant acetyl xylan esterase 873B3 having the following substitutions relative to the wild-type *Thermotoga maritima* acetyl xylan esterase amino acid sequence: A266N/C277S.

SEQ ID NO: 110 is the amino acid sequence of the 873B3 variant acetyl xylan esterase.

SEQ ID NO: 111 is the nucleic acid sequence encoding the variant acetyl xylan esterase 873B12 having the following substitutions relative to the wild-type *Thermotoga maritime* acetyl xylan esterase amino acid sequence: A266R/C277S.

SEQ ID NO: 112 is the amino acid sequence of the 873B12 variant acetyl xylan esterase.

SEQ ID NO: 113 is the nucleic acid sequence encoding the variant acetyl xylan esterase 873G3 having the following substitutions relative to the wild-type *Thermotoga maritime* acetyl xylan esterase amino acid sequence: A266Q/C277S.

SEQ ID NO: 114 is the amino acid sequence of the 873G3 variant acetyl xylan esterase.

SEQ ID NO: 115 is the nucleic acid sequence encoding the variant acetyl xylan esterase 873E2 having the following substitutions relative to the wild-type *Thermotoga maritime* acetyl xylan esterase amino acid sequence: A266V/C277S.

SEQ ID NO: 116 is the amino acid sequence of the 873E2 variant acetyl xylan esterase.

DETAILED DESCRIPTION

A nucleic acid molecule encoding the *Thermotoga maritime* C277T variant acetyl xylan esterase (SEQ ID NO: 5) was mutated to create a library of variant perhydrolases. Several perhydrolase variants were identified exhibiting an increase in specific activity when compared to the specific activity of the *Thermotoga maritime* C277T perhydrolase having amino acid sequence SEQ ID NO: 5.

A library of variant perhydrolases was also created using site saturation mutagenesis of the *Thermotoga maritime* variant acetyl xylan esterase C277S (SEQ ID NO: 69) at residues S25, K77, L125M, A266, N275, and N302. A perhydrolase variant was identified exhibiting an increase in specific activity when compared to the specific activity of the *Thermotoga maritima* C277S perhydrolase having amino acid sequence SEQ ID NO: 69.

Compositions and methods are provided comprising the variant perhydrolase enzyme having amino acid sequence SEQ ID NO: 30.

In this disclosure, a number of terms and abbreviations are used. The following definitions apply unless specifically stated otherwise.

As used herein, the articles “a”, “an”, and “the” preceding an element or component of the invention are intended to be nonrestrictive regarding the number of instances (i.e., occurrences) of the element or component. Therefore “a”, “an” and “the” should be read to include one or at least one, and the singular word form of the element or component also includes the plural unless the number is obviously meant to be singular.

The term “comprising” means the presence of the stated features, integers, steps, or components as referred to in the claims, but does not preclude the presence or addition of one or more other features, integers, steps, components or groups thereof. The term “comprising” is intended to include embodiments encompassed by the terms “consisting essentially of” and “consisting of”. Similarly, the term “consisting essentially of” is intended to include embodiments encompassed by the term “consisting of”.

As used herein, the term “about” modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term “about” also encompasses amounts that differ due to different equilibrium conditions for a composition resulting from a particular initial mixture. Whether or not modified by the term “about”, the claims include equivalents to the quantities.

Where present, all ranges are inclusive and combinable. For example, when a range of “1 to 5” is recited, the recited range should be construed as including ranges “1 to 4”, “1 to 3”, “1-2”, “1-2 & 4-5”, “1-3 & 5”, and the like.

As used herein, the term “multi-component system” will refer to a system of enzymatically generating peroxycarboxylic acid wherein the components remain separated until use. As such, the multi-component system will include at least one first component that remains separated from at least one second component. The first and second components are separated in different compartments until use (i.e., using first and second compartments). The design of the multi-component systems will often depend on the physical form of the components to be combined and are described in more detail below.

As used herein, the term “peroxycarboxylic acid” is synonymous with peracid, peroxyacid, peroxy acid, percarboxylic acid and peroxoic acid.

As used herein, the term “peracetic acid” is abbreviated as “PAA” and is synonymous with peroxyacetic acid, ethaneperoxoic acid and all other synonyms of CAS Registry Number 79-21-0.

As used herein, the term “monoacetin” is synonymous with glycerol monoacetate, glycerin monoacetate, and glyceryl monoacetate.

As used herein, the term “diacetin” is synonymous with glycerol diacetate; glycerin diacetate, glyceryl diacetate, and all other synonyms of CAS Registry Number 25395-31-7.

As used herein, the term “triacetin” is synonymous with glycerin triacetate; glycerol triacetate; glyceryl triacetate, 1,2,3-triacetoxypropane, 1,2,3-propanetriol triacetate and all other synonyms of CAS Registry Number 102-76-1.

As used herein, the term “monobutyrin” is synonymous with glycerol monobutyrate, glycerin monobutyrate, and glyceryl monobutyrate.

As used herein, the term “dibutyrin” is synonymous with glycerol dibutyrate and glyceryl dibutyrate.

As used herein, the term “tributyrin” is synonymous with glycerol tributyrate, 1,2,3-tributyrylglycerol, and all other synonyms of CAS Registry Number 60-01-5.

As used herein, the term “monopropionin” is synonymous with glycerol monopropionate, glycerin monopropionate, and glyceryl monopropionate.

As used herein, the term “dipropionin” is synonymous with glycerol dipropionate and glyceryl dipropionate.

As used herein, the term “tripropionin” is synonymous with glyceryl tripropionate, glycerol tripropionate, 1,2,3-tripropionylglycerol, and all other synonyms of CAS Registry Number 139-45-7.

As used herein, the term “ethyl acetate” is synonymous with acetic ether, acetoxyethane, ethyl ethanoate, acetic acid ethyl ester, ethanoic acid ethyl ester, ethyl acetic ester and all other synonyms of CAS Registry Number 141-78-6.

As used herein, the term “ethyl lactate” is synonymous with lactic acid ethyl ester and all other synonyms of CAS Registry Number 97-64-3.

As used herein, the terms “acylated sugar” and “acylated saccharide” refer to mono-, di- and polysaccharides comprising at least one acyl group, where the acyl group is selected from the group consisting of straight chain aliphatic carboxylates having a chain length from C2 to C8. Examples include, but are not limited to, glucose pentaacetate, xylose tetraacetate, acetylated xylan, acetylated xylan fragments, β-D-ribofuranose-1,2,3,5-tetraacetate, tri-O-acetyl-D-galactal, and tri-O-acetyl-glucal.

As used herein, the terms “hydrocarbyl”, “hydrocarbyl group”, and “hydrocarbyl moiety” mean a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In one embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the term "aromatic" refers to an organic compound or moiety characterized by increased chemical stability resulting from the delocalization of electrons in a ring system containing usually multiple conjugated double bonds. Planar monocyclic conjugated rings having delocalized electrons should be aromatic if the have $(4n+2)\pi$ electrons. Examples of aromatic compounds may include derivatives of benzene (such as 2-, 3- or 4-acetoxybenzoic acid). In one embodiment, the ester substrate may be 4-acetoxybenzoic acid.

As used herein, the term "heterocyclic" refers to an organic compound or moiety with a ring structure having one or more atoms other than carbon in at least one of its rings.

As used herein, the term "heteroaromatic" refers to an organic compound or moiety with a ring structure that is both heterocyclic and aromatic, wherein the ring comprises at least one of the heteroatoms oxygen, nitrogen, or sulfur. Examples of heteroaromatic moieties may include pyridine, pyrrole, furan, and thiophene moieties.

As used herein, the terms "monoesters" and "diesters" of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol, refer to said compounds comprising at least one ester group of the formula RC(O)O, wherein R is a C1 to C7 linear hydrocarbyl moiety.

As used herein, the terms "suitable enzymatic reaction formulation", "components suitable for generation of a peroxycarboxylic acid", "suitable reaction components", "reaction components", "reaction formulation", and "suitable aqueous reaction formulation" refer to the materials and water in which the reactants and the enzyme catalyst comprising the present variant polypeptide having perhydrolytic activity come into contact to form the desired peroxycarboxylic acid. The components of the reaction formulation are provided herein and those skilled in the art appreciate the range of component variations suitable for this process. In one embodiment, the enzymatic reaction formulation produces peroxycarboxylic acid in situ upon combining the reaction components. As such, the reaction components may be provided as a multi-component system wherein one or more of the reaction components remains separated until use. The design of systems and means for separating and combining multiple active components are known in the art and generally will depend upon the physical form of the individual reaction components. For example, multiple active fluids (liquid-liquid) systems typically use multi-chamber dispenser bottles or two-phase systems (U.S. Patent Application Publication No. 2005-0139608; U.S. Pat. Nos. 5,398,846; 5,624,634; 6,391,840; E.P. Patent 0807156B1; U.S. Patent Application Publication No. 2005-0008526; and PCT Publication No. WO 00/61713A1) such as found in some bleaching applications wherein the desired bleaching agent is produced upon mixing the reactive fluids. Multi-component formulations and multi-component generation systems to enzymatically produce peroxycarboxylic acids from carboxylic acid esters are described by DiCosimo et al. in Published U.S Patent Application Nos. 2010-0086510 and 2010-0086621, respectively. Other forms of multi-component systems used to generate peroxycarboxylic acid may include, but are not limited to, those designed for one or more solid components or combinations of solid-liquid components, such as powders used in many commercially available bleaching compositions (e.g., U.S. Pat. No. 5,116,575), multi-layered tablets (e.g., U.S. Pat. No. 6,210,639), water dissolvable packets having multiple compartments (e.g., U.S. Pat. No. 6,995,125) and solid agglomerates that react upon the addition of water (e.g., U.S. Pat. No. 6,319,888).

As used herein, the term "substrate" or "carboxylic acid ester substrate" will refer to the reaction components enzymatically perhydrolyzed using the present enzyme catalyst in the presence of a suitable source of peroxygen, such as hydrogen peroxide. In one embodiment, the substrate comprises at least one ester group capable of being enzymatically perhydrolyzed using the enzyme catalyst, whereby a peroxycarboxylic acid is produced.

As used herein, the term "perhydrolysis" is defined as the reaction of a selected substrate with a source of hydrogen peroxide to form a peroxycarboxylic acid. Typically, inorganic peroxide is reacted with the selected substrate in the presence of a catalyst to produce the peroxycarboxylic acid. As used herein, the term "chemical perhydrolysis" includes perhydrolysis reactions in which a substrate (such as a peroxycarboxylic acid precursor) is combined with a source of hydrogen peroxide wherein peroxycarboxylic acid is formed in the absence of an enzyme catalyst. As used herein, the term "enzymatic perhydrolysis" refers a reaction of a selected substrate with a source of hydrogen peroxide to form a peroxycarboxylic acid, wherein the reaction is catalyzed by an enzyme catalyst having perhydrolysis activity.

As used herein, the term "perhydrolase activity" refers to the enzyme catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 μmol of peroxycarboxylic acid product (such as peracetic acid) per minute at a specified temperature. "One unit of enzyme activity" may also be used herein to refer to the amount of peroxycarboxylic acid hydrolysis activity required for the hydrolysis of 1 μmol of peroxycarboxylic acid (e.g., peracetic acid) per minute at a specified temperature.

The present variant CE-7 carbohydrate esterase is characterized by an increase in specific activity when compared to the perhydrolase from which it was derived (*Thermotoga maritime* C277T; Published U.S. Patent Application No. 2010-0087529) under the same reaction conditions. As used herein, the "fold increase" in specific activity is measured relative to the specific activity of the parent perhydrolase from which the variant was derived (either the *Thermotoga maritime* C277T perhydrolase (SEQ ID NO: 5) or *Thermotoga maritime* C277S perhydrolase (SEQ ID NO: 69)) under the same reaction conditions. In one embodiment, the fold increase in specific activity of the variant polypeptide (i.e., variant perhydrolase) relative to the parent perhydrolase (*Thermotoga maritime* C277T or C277S) is at least 1.01, 1.05, 1.1, 1.2, 1.3, 1.4, 1.5, 1.6, 1.7, 1.8, 1.9., 2.0, 3.0, 4.0, 5.0, 6.0, 7.0, 8.0, 9.0, or 10-fold when compared under identical reaction/assay conditions.

As used herein, "identical assay conditions" or "same assay conditions" refer to the conditions used to measure the peracid formation (i.e., perhydrolysis of a carboxylic acid ester substrate) specific activity of the variant polypeptide relative to the respective specific activity of the polypeptide from which it is was derived. The assay conditions used to measure the respective specific activities should be as close to identical as possible such that only the structure of the polypeptide having perhydrolytic activity varies.

As used herein, the terms "enzyme catalyst" and "perhydrolase catalyst" refer to a catalyst comprising an enzyme (i.e., a polypeptide) having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (for example, by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997.

The present enzyme catalyst comprises a variant polypeptide having perhydrolytic activity and is structurally classified as a member of the carbohydrate family esterase family 7 (CE-7 family) of enzymes (see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.). The CE-7 family of enzymes has been demonstrated to be particularly effective for producing peroxycarboxylic acids from a variety of carboxylic acid ester substrates when combined with a source of peroxygen (See PCT publication No. WO2007/070609 and U.S. Patent Application Publication No. 2008-0176299 and U.S. Pat. Nos. 7,951,566 and 7,723,083 to DiCosimo et al.; each herein incorporated by reference in their entireties). The CE-7 enzyme family includes cephalosporin C deacetylases (CAHs; E.C. 3.1.1.41) and acetyl xylan esterases (AXEs; E.C. 3.1.1.72). Members of the CE-7 enzyme family share a conserved signature motif (Vincent et al., *J. Mol. Biol.,* 330:593-606 (2003)).

As used herein, the terms "signature motif" and "CE-7 signature motif", refer to conserved structures shared among a family of enzymes having a perhydrolytic activity.

As used herein, "structurally classified as a CE-7 enzyme", "structurally classified as a carbohydrate esterase family 7 enzyme", "structurally classified as a CE-7 carbohydrate esterase", and "CE-7 perhydrolase" will be used to refer to enzymes having perhydrolysis activity that are structurally classified as a CE-7 carbohydrate esterase based on the presence of the CE-7 signature motif (Vincent et al., supra). The "signature motif" for CE-7 esterases comprises three conserved motifs (residue position numbering relative to reference sequence SEQ ID NO: 2; the wild-type *Thermotoga maritime* acetyl xylan esterase):

a) Arg118-Gly119-Gln120;

b) Gly186-Xaa187-Ser188-Gln189-Gly190; and c) His303-Glu304.

Typically, the Xaa at amino acid residue position 187 is glycine, alanine, proline, tryptophan, or threonine. Two of the three amino acid residues belonging to the catalytic triad are in bold. In one embodiment, the Xaa at amino acid residue position 187 is selected from the group consisting of glycine, alanine, proline, tryptophan, and threonine.

Further analysis of the conserved motifs within the CE-7 carbohydrate esterase family indicates the presence of an additional conserved motif (LXD at amino acid positions 272-274 of SEQ ID NO: 2) that may be used to further define a member of the CE-7 carbohydrate esterase family. In a further embodiment, the signature motif defined above includes a fourth conserved motif defined as:

Leu272-Xaa273-Asp274.

The Xaa at amino acid residue position 273 is typically isoleucine, valine, or methionine. The fourth motif includes the aspartic acid residue (bold) belonging to the catalytic triad (Ser188-Asp274-His303).

As used herein, the terms "cephalosporin C deacetylase" and "cephalosporin C acetyl hydrolase" refer to an enzyme (E.G. 3.1.1.41) that catalyzes the deacetylation of cephalosporins such as cephalosporin C and 7-aminocephalosporanic acid (Mitsushima et al., *Appl. Environ. Microbiol.,* 61(6): 2224-2229 (1995); U.S. Pat. Nos. 5,528,152; and 5,338,676). Enzymes classified as cephalosporin C deacetylases have been shown to often have significant perhydrolytic activity (U.S. Pat. No. 7,951,566 and U.S. Patent Application Publication No. 2008-0176299 to DiCosimo et al.).

As used herein, "acetyl xylan esterase" refers to an enzyme (E.C. 3.1.1.72; AXEs) that catalyzes the deacetylation of acetylated xylans and other acetylated saccharides. Enzymes classified as acetyl xylan esterases have been shown to have significant perhydrolytic activity (U.S. Pat. Nos. 7,951,566 and 7,723,083 and U.S. Patent Application Publication No. 2008-0176299, each to DiCosimo et al.).

As used herein, the term "*Thermotoga maritima*" refers to a bacterial cell reported to have acetyl xylan esterase activity (GENBANK® NP_227893.1). In one aspect, the *Thermotoga maritima* strain is *Thermotoga maritima* MSB8. The amino acid sequence of the wild-type enzyme having perhydrolase activity from *Thermotoga maritime* is provided as SEQ ID NO: 2.

As used herein, the terms "variant", "variant polypeptide", and "variant enzyme catalyst" refer to an enzyme catalyst comprising at least one polypeptide (i.e., a perhydrolase) having perhydrolytic activity wherein the polypeptide comprises at least one amino acid change relative to the enzyme/polypeptide from which it was derived (i.e., *Thermotoga maritima* C277S or C277T perhydrolase). Several variant polypeptides are provided herein having perhydrolytic activity and are characterized by an increase in specific activity relative to the *Thermotoga maritima* C277T acetyl xylan esterase having amino acid sequence SEQ ID NO: 5. A variant polypeptide having an increase in perhydrolytic specific activity relative to the *Thermotoga maritime* C277S (SEQ ID NO: 69) is also provided (Published U.S. Patent Application No. 2010-0087529 and U.S. patent application Ser. No. 13/070,123).

For a particular variant perhydrolase, amino acid substitutions are specified with reference to the wild type *Thermotoga maritima* amino acid sequence (SEQ ID NO: 2). The wild-type amino acid (denoted by the standard single letter abbreviation) is followed by the amino acid residue position of SEQ ID NO: 2 followed by the amino acid of the variant (also denoted by the standard single letter abbreviation). For example, "C277S" describes a change in SEQ ID NO: 2 at amino acid residue position 277 where cysteine was changed to serine. The variant polypeptide may be comprised of multiple point substitutions. For example, R261S/I264F/C277T refers to a variant polypeptide having three point substitutions: 1) a change at amino acid residue position 261 where an arginine was changed to a serine, 2) a change at residue position 264 where an isoleucine was changed to a phenylalanine, and 3) a change at position 277 where a cysteine was changed to a threonine.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid (or as defined herein) | Xaa | X |

As used herein, the term "biological contaminants" refers to one or more unwanted and/or pathogenic biological entities including, but not limited to microorganisms, spores, viruses, prions, and mixtures thereof. The present enzyme can be used to produce an efficacious concentration of at least one peroxycarboxylic acid useful to reduce and/or eliminate the presence of the viable biological contaminants. In a preferred embodiment, the biological contaminant is a viable pathogenic microorganism.

As used herein, the term "disinfect" refers to the process of destruction of or prevention of the growth of biological contaminants. As used herein, the term "disinfectant" refers to an agent that disinfects by destroying, neutralizing, or inhibiting the growth of biological contaminants. Typically, disinfectants are used to treat inanimate objects or surfaces. As used herein, the term "antiseptic" refers to a chemical agent that inhibits the growth of disease-carrying microorganisms. In one aspect of the embodiment, the biological contaminants are pathogenic microorganisms.

As used herein, the term "sanitary" means of or relating to the restoration or preservation of health, typically by removing, preventing or controlling an agent that may be injurious to health. As used herein, the term "sanitize" means to make sanitary. As used herein, the term "sanitizer" refers to a sanitizing agent. As used herein the term "sanitization" refers to the act or process of sanitizing.

As used herein, the term "virucide" refers to an agent that inhibits or destroys viruses, and is synonymous with "viricide". An agent that exhibits the ability to inhibit or destroy viruses is described as having "virucidal" activity. Peroxycarboxylic acids can have virucidal activity. Typical alternative virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peroxycarboxylic acids can have biocidal activity. Typical alternative biocides known in the art, which may be suitable for use in the present invention include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $\log_{10}$ reduction in viable microorganisms after treatment. In one aspect, the targeted reduction in viable microorganisms after treatment is at least a 3-$\log_{10}$ reduction, more preferably at least a 4-$\log_{10}$ reduction, and most preferably at least a 5-$\log_{10}$ reduction. In another aspect, the minimum biocidal concentration is at least a 6-$\log_{10}$ reduction in viable microbial cells.

As used herein, the terms "peroxygen source" and "source of peroxygen" refer to compounds capable of providing hydrogen peroxide at a concentration of about 1 mM or more when in an aqueous solution including, but not limited to, hydrogen peroxide, hydrogen peroxide adducts (e.g., urea-hydrogen peroxide adduct (carbamide peroxide)), perborates, and percarbonates, such as sodium percarbonate. As described herein, the concentration of the hydrogen peroxide provided by the peroxygen compound in the aqueous reaction formulation is initially at least 1 mM or more upon combining the reaction components. In one embodiment, the hydrogen peroxide concentration in the aqueous reaction formulation is at least 0.5 mM. In another embodiment, the hydrogen peroxide concentration in the aqueous reaction formulation is at least 10 mM. In another embodiment, the hydrogen peroxide concentration in the aqueous reaction formulation is at least 100 mM. In another embodiment, the hydrogen peroxide concentration in the aqueous reaction formulation is at least 200 mM. In another embodiment, the hydrogen peroxide concentration in the aqueous reaction formulation is 500 mM or more. In yet another embodiment, the hydrogen peroxide concentration in the aqueous reaction formulation is 1000 mM or more. The molar ratio of the hydrogen peroxide to enzyme substrate, such as triglyceride, ($H_2O_2$:substrate) in the aqueous reaction formulation may be from about 0.002 to 20, preferably about 0.1 to 10, and most preferably about 0.5 to 5.

As used herein, the term "benefit agent" refers to a material that promotes or enhances a useful advantage, a favorable/desirable effect or benefit. In one embodiment, a process is provided whereby a benefit agent, such as a composition comprising a peroxycarboxylic acid, is applied to a textile or article of clothing to achieve a desired benefit, such as disinfecting, bleaching, destaining, deodorizing, and any combination thereof. In another embodiment, the present variant polypeptide having perhydrolytic activity may be used to produce a peracid-based benefit agent for use in personal care products (such as hair care products, skin care products, nail care products or oral care products). In one embodiment, a personal care product is provided comprising the variant perhydrolase having amino acid sequence SEQ ID NO: 30. The personal care products are formulated to provide a safe and efficacious concentration of the desired peracid benefit agent.

Variant Polypeptides Having an Increase in Specific Activity.

The present variant polypeptides were derived from the *Thermotoga maritime* C277S or *Thermotoga maritime* C277T acetyl xylan esterase that has been previously demonstrated to have significant perhydrolytic activity for producing peroxycarboxylic acids from carboxylic acid esters and a source of peroxygen, such as hydrogen peroxide (U.S.

Patent Application Publication No. 2008-0176299 and 2010-0087529, each to DiCosimo et al.).

Libraries of variant polypeptides were created from the C277T *Thermotoga maritime* perhydrolase (SEQ ID NO: 5) or the *Thermotoga maritime* C277S perhydrolase (SEQ ID NO: 69) and assayed for an increase in the specific activity for producing peroxycarboxylic acids from carboxylic acid ester substrates. The assay conditions used to measure the respective specific activities should be as close to identical as possible such that only the structure of the polypeptide having perhydrolytic activity varies. In one embodiment, reactions used to measure specific activity are run at ca. 25° C. in sodium bicarbonate buffer (10 mM, pH 6.5) containing 2 mM triacetin, 10 mM hydrogen peroxide and approximately 2.0 μg/mL of heat-treated extract supernatant total protein from *E. coli* strain KLP18 expressing the C277T or C277S perhydrolase or variant perhydrolase, optionally in the presence of 2 mg/mL liquid laundry detergent (comprising 15-30% anionic and non-ionic surfactants, 5-15% soap, and <5% polycarboxylates, perfume, phosphonates, optical brighteners; see Example 7).

In another embodiment, the reactions to measure specific activity are conducted under simulated laundry care conditions at ca. 20° C. using 0 to 6 mg/mL liquid laundry detergent, 2 mM triacetin, 10 mM hydrogen peroxide (from sodium percarbonate), hard water plus percarbonate as a buffer (pH 10), and 2 μg/mL to 6 μg/mL of heat-treated extract supernatant total soluble protein from *E. coli* strain KLP18 expressing the *T. maritima* C277T or C277S perhydrolase or the present variant perhydrolase (see Example 8).

In another embodiment, the reactions to measure specific activity are conducted under simulated laundry care conditions at ca. 20° C. using 0 to 6 mg/mL liquid laundry detergent, 1 mM triacetin, 4.4 mM hydrogen peroxide (from sodium percarbonate), hard water plus percarbonate as a buffer (pH 9), and 1 μg/mL to 6 μg/mL of heat-treated extract supernatant total soluble protein from *E. coli* strain KLP18 expressing the *T. maritima* C277T or C2775 perhydrolase or the present variant perhydrolase (see Example 9).

In another embodiment, the reactions to measure specific activity are conducted at ca. 20° C. using 0 to 6 mg/mL liquid laundry detergent, 2 mM 4-acetoxybenozoic acid (4ABA), 10 mM hydrogen peroxide (from sodium percarbonate), in sodium percarbonate buffer (pH 7), and 2 μg/mL to 6 μg/mL of heat-treated extract supernatant total soluble protein from *E. coli* strain KLP18 expressing the *T. maritima* C277T or C2775 perhydrolase or the present variant perhydrolase (see Example 10).

In another embodiment, the reactions to measure specific activity are conducted under simulated laundry care conditions at ca. 25° C. using about 2 g/L solid laundry detergent, a formulation generally comprising a mixture of surfactants (sodium dodecylbenzenesulfonate, C12-15 Pareth-5, C12-15 Pareth-7, sodium stearate, and stearic acid), builders (sodium carbonate, zeolite, sodium silicate, and citric acid), binders (cellulose, PEG-75, dextrin, and sucrose), bulking agents (sodium sulfate, sodium chloride, sodium bicarbonate, and calcium carbonate), structurants (sodium acrylic Acid/MA copolymer, and sodium polyacrylate), sequestrants (tetrasodium etidronate and calcium sodium EDTMP), optical brighteners (disodium anilinomorpholinotriazinylaminostilbenesulfonate), stabilizing agents, anti-redeposition agents, antifoaming agents, and softness extenders, 0.5 mM triacetin, 2 mM $H_2O_2$ from sodium perborate in deionized water, and about 2.0 μg/mL of heat-treated extract supernatant total soluble protein from *E. coli* strain KLP18 (as prepare in Example 6) expressing the *T. maritima* C277T or C277S perhydrolase or the present variant perhydrolase (see Example 11).

Suitable Reaction Conditions for the Enzyme-catalyzed Preparation of Peroxycarboxylic Acids from Carboxylic Acid Esters and Hydrogen Peroxide A process is provided to produce an aqueous formulation comprising at least one peroxycarboxylic acid by reacting carboxylic acid esters and an inorganic peroxide (such as hydrogen peroxide, sodium perborate or sodium percarbonate) in the presence of an enzyme catalyst having perhydrolysis activity, wherein the enzyme catalyst comprises, in one embodiment, a polypeptide having an amino acid sequence selected from the group consisting of SEQ ID NOs: 12, 14, 16, 30, 34, 40, 46, and 102. In a further embodiment, the polypeptide has the amino acid sequence of SEQ ID NO: 30.

In one embodiment, suitable substrates include one or more esters provided by the following formula:

$$[X]_m R_5$$

wherein X=an ester group of the formula $R_6C(O)O$ $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m=is an integer ranging from 1 to the number of carbon atoms in $R_5$; and wherein said esters have solubility in water of at least 5 ppm at 25° C.

In another embodiment, $R_6$ is C1 to C7 linear hydrocarbyl moiety, optionally substituted with hydroxyl groups or C1 to C4 alkoxy groups, optionally comprising one or more ether linkages. In a further preferred embodiment, $R_6$ is C2 to C7 linear hydrocarbyl moiety, optionally substituted with hydroxyl groups, and/or optionally comprising one or more ether linkages.

In one embodiment, the suitable substrate may include 2-acetoxybenzoic acid, 3-acetoxybenzoic acid, 4-acetoxybenzoic acid or mixtures thereof.

In another embodiment, suitable substrates also include one or more glycerides of the formula:

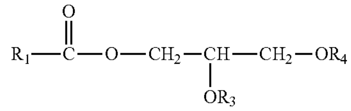

wherein $R_1$=C1 to C21 straight chain or branched chain alkyl optionally substituted with an hydroxyl or a C1 to C4 alkoxy group and $R_3$ and $R_4$ are individually H or $R_1C(O)$. In one embodiment, the suitable substrate is a glyceride of the above formula wherein $R_1$=C1 to C7 straight chain or branched chain alkyl optionally substituted with an hydroxyl or a C1 to C4 alkoxy group and $R_3$ and $R_4$ are individually H or $R_1C(O)$.

In another aspect, suitable substrates may also include one or more esters of the formula:

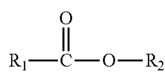

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10.

Suitable substrates may also include one or more acylated saccharides selected from the group consisting of acylated mono-, di-, and polysaccharides. In another embodiment, the acylated saccharides are selected from the group consisting of acetylated xylan, fragments of acetylated xylan, acetylated xylose (such as xylose tetraacetate), acetylated glucose (such as α-D-glucose pentaacetate; β-D-glucose pentaacetate), β-D-galactose pentaacetate, sorbitol hexaacetate, sucrose octaacetate, β-D-ribofuranose-1,2,3,5-tetraacetate, tri-O-acetyl-D-galactal, tri-O-acetyl-D-glucal, and acetylated cellulose. In a preferred embodiment, the acetylated saccharide is selected from the group consisting of β-D-ribofuranose-1,2,3,5-tetraacetate, tri-O-acetyl-D-galactal, tri-O-acetyl-D-glucal, and acetylated cellulose.

In another embodiment, suitable substrates are selected from the group consisting of: monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-D-glucal; monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol; and mixtures thereof.

In another embodiment, the carboxylic acid ester is selected from the group consisting of monoacetin, diacetin, triacetin, and combinations thereof. In another embodiment, the substrate is a C1 to C6 polyol comprising one or more ester groups. In a preferred embodiment, one or more of the hydroxyl groups on the C1 to C6 polyol are substituted with one or more acetoxy groups (such as 1,3-propanediol diacetate, 1,4-butanediol diacetate, etc.). In a further embodiment, the substrate is propylene glycol diacetate (PGDA), ethylene glycol diacetate (EGDA), or a mixture thereof.

In another embodiment, suitable substrates are selected from the group consisting of ethyl acetate; methyl lactate; ethyl lactate; methyl glycolate; ethyl glycolate; methyl methoxyacetate; ethyl methoxyacetate; methyl 3-hydroxybutyrate; ethyl 3-hydroxybutyrate; triethyl 2-acetyl citrate; glucose pentaacetate; gluconolactone; glycerides (mono-, di-, and triglycerides) such as monoacetin, diacetin, triacetin, monopropionin, dipropionin (glyceryl dipropionate), tripropionin (1,2,3-tripropionylglycerol), monobutyrin, dibutyrin (glyceryl dibutyrate), tributyrin (1,2,3-tributyrylglycerol); acetylated saccharides; and mixtures thereof.

In a further embodiment, suitable substrates are selected from the group consisting of monoacetin, diacetin, triacetin, monopropionin, dipropionin, tripropionin, monobutyrin, dibutyrin, tributyrin, ethyl acetate, and ethyl lactate. In yet another aspect, the substrate is selected from the group consisting of diacetin, triacetin, ethyl acetate, and ethyl lactate. In a most preferred embodiment, the suitable substrate comprises triacetin.

The carboxylic acid ester is present in the aqueous reaction formulation at a concentration sufficient to produce the desired concentration of peroxycarboxylic acid upon enzyme-catalyzed perhydrolysis. The carboxylic acid ester need not be completely soluble in the aqueous reaction formulation, but has sufficient solubility to permit conversion of the ester by the perhydrolase catalyst to the corresponding peroxycarboxylic acid. The carboxylic acid ester is present in the aqueous reaction formulation at a concentration of 0.0005 wt % to 40 wt % of the aqueous reaction formulation, preferably at a concentration of 0.01 wt % to 20 wt % of the aqueous reaction formulation, and more preferably at a concentration of 0.05 wt % to 10 wt % of the aqueous reaction formulation. The wt % of carboxylic acid ester may optionally be greater than the solubility limit of the carboxylic acid ester, such that the concentration of the carboxylic acid ester is at least 0.0005 wt % in the aqueous reaction formulation that is comprised of water, enzyme catalyst, and source of peroxide, where the remainder of the carboxylic acid ester remains as a second separate phase of a two-phase aqueous/organic reaction formulation. Not all of the added carboxylic acid ester must immediately dissolve in the aqueous reaction formulation, and after an initial mixing of all reaction components, additional continuous or discontinuous mixing is optional.

The peroxycarboxylic acids produced by the present reaction components may vary depending upon the selected substrates, so long as the present enzyme catalyst is used. In one embodiment, the peroxycarboxylic acid produced is peracetic acid, perpropionic acid, perbutyric acid, peroctanoic acid, perlactic acid, perglycolic acid, permethoxyacetic acid, per-β-hydroxybutyric acid, or mixtures thereof.

The peroxygen source may include, but is not limited to, hydrogen peroxide, hydrogen peroxide adducts (e.g., urea-hydrogen peroxide adduct (carbamide peroxide)), perborate salts and percarbonate salts. Alternatively, hydrogen peroxide can be generated in situ by the reaction of a substrate and oxygen catalyzed by an enzyme having oxidase activity (including, but not limited to, glucose oxidase, galactose oxidase, sorbitol oxidase, hexose oxidase, alcohol oxidase, glycerol oxidase, monoamine oxidase, glycolate oxidase, lactate oxidase, pyruvate oxidase, oxalate oxidase, choline oxidase, cholesterol oxidase, pyranose oxidase, carboxyalcohol oxidase, L-amino acid oxidase, glycine oxidase, glutamate oxidase, lysine oxidase, and uricase). The concentration of peroxygen compound in the aqueous reaction formulation may range from 0.0033 wt % to about 50 wt %, preferably from 0.033 wt % to about 40 wt %, more preferably from 0.33 wt % to about 30 wt %.

Many perhydrolase catalysts (such as whole cells, permeabilized whole cells, and partially purified whole cell extracts) have been reported to have catalase activity (EC 1.11.1.6). Catalases catalyze the conversion of hydrogen peroxide into oxygen and water. In one aspect, the enzyme catalyst having perhydrolase activity lacks catalase activity. In another aspect, the enzyme catalyst having perhydrolase activity has a sufficiently-low catalase activity that the presence of said catalase activity does not significantly interfere with perhydrolase-catalyzed peroxycarboxylic acid production. In another aspect, a catalase inhibitor is added to the aqueous reaction formulation. Examples of catalase inhibitors include, but are not limited to, sodium azide and hydroxylamine sulfate. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM. In one aspect, sodium azide concentration typically ranges from about 20 mM to about 60 mM while hydroxylamine sulfate is concentration is typically about 0.5 mM to about 30 mM, preferably about 10 mM.

The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis. In a preferred embodiment, the gene(s) encoding the endogenous catalase activity are down-regulated or disrupted (i.e., "knocked-out"). As used herein, a "disrupted" gene is one where the activity and/or function of the protein encoded by the modified gene is no longer present. Means to disrupt a gene are well-known in the art and may include, but are not limited to, insertions, deletions, or mutations to the gene so long as the activity and/or function of the corresponding protein is no longer present. In a further preferred embodiment, the production host is an *E. coli* production host comprising a disrupted catalase gene selected from the group consisting of katG and katE (see U.S. Pat. No. 7,951,566 to DiCosimo et al.). In another embodiment, the production host is an *E. coli* strain comprising a down-regulation and/or disruption in both katG and katE catalase genes. An *E. coli* strain comprising a double-knockout of katG and katE has been prepared and is described as *E. coli* strain KLP18 (U.S. Pat. No. 7,951,566 to DiCosimo et al.).

The concentration of the catalyst in the aqueous reaction formulation depends on the specific catalytic activity of the catalyst, and is chosen to obtain the desired rate of reaction. The weight of catalyst in perhydrolysis reactions typically ranges from 0.0001 mg to 50 mg per mL of total reaction volume, preferably from 0.0005 mg to 10 mg per mL, more preferably from 0.0010 mg to 2.0 mg per mL. The catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, and mixtures thereof.

In one aspect, the concentration of peroxycarboxylic acid generated by the combination of chemical perhydrolysis and enzymatic perhydrolysis of the carboxylic acid ester is sufficient to provide an effective concentration of peroxycarboxylic acid for disinfection, bleaching, sanitization, deodorizing or destaining at a desired pH. In another aspect, the peroxycarboxylic acid is generated at a safe and efficacious concentration suitable for use in a personal care product to be applied to the hair, skin, nails or tissues of the oral cavity, such as tooth enamel, tooth pellicle or the gums. In another aspect, the present methods provide combinations of enzymes and enzyme substrates to produce the desired effective concentration of peroxycarboxylic acid, where, in the absence of added enzyme, there is a significantly lower concentration of peroxycarboxylic acid produced. Although there may be some chemical perhydrolysis of the enzyme substrate by direct chemical reaction of inorganic peroxide with the enzyme substrate, there may not be a sufficient concentration of peroxycarboxylic acid generated to provide an effective concentration of peroxycarboxylic acid in the desired applications, and a significant increase in total peroxycarboxylic acid concentration is achieved by the addition of an appropriate perhydrolase catalyst to the aqueous reaction formulation.

In one aspect of the invention, the concentration of peroxycarboxylic acid generated (e.g. peracetic acid) by the enzymatic perhydrolysis is at least about 2 ppm, preferably at least 20 ppm, preferably at least 100 ppm, more preferably at least about 200 ppm peroxycarboxylic acid, more preferably at least 300 ppm, more preferably at least 500 ppm, more preferably at least 700 ppm, more preferably at least about 1000 ppm peroxycarboxylic acid, more preferably at least about 2000 ppm peroxycarboxylic acid, most preferably at least 10,000 ppm peroxycarboxylic acid within 5 minutes more preferably within 1 minute of initiating the enzymatic perhydrolysis reaction. In a second aspect of the invention, the concentration of peroxycarboxylic acid generated (e.g. peracetic acid) by the enzymatic perhydrolysis is at least about 2 ppm, preferably at least 20 ppm, preferably at least 30 ppm, more preferably at least about 40 ppm peroxycarboxylic acid, more preferably at least 50 ppm, more preferably at least 60 ppm, more preferably at least 70 ppm, more preferably at least about 80 ppm peroxycarboxylic acid, most preferably at least 100 ppm peroxycarboxylic acid within 5 minutes, more preferably within 1 minute, of initiating the enzymatic perhydrolysis reaction (i.e., time measured from combining the reaction components to form the formulation).

The aqueous formulation comprising the peroxycarboxylic acid may be optionally diluted with diluent comprising water, or a solution predominantly comprised of water, to produce a formulation with the desired lower target concentration of peroxycarboxylic acid. In one aspect, the reaction time required to produce the desired concentration (or concentration range) of peroxycarboxylic acid is about 20 minutes or less, preferable about 5 minutes or less, most preferably about 1 minute or less.

In other aspects, the surface or inanimate object contaminated with a concentration of a biological contaminant(s) is contacted with the peroxycarboxylic acid formed in accordance with the processes described herein within about 1 minute to about 168 hours of combining said reaction components, or within about 1 minute to about 48 hours, or within about 1 minute to 2 hours of combining said reaction components, or any such time interval therein.

In another aspect, the peroxycarboxylic acid formed in accordance with the processes describe herein is used in a laundry care application wherein the peroxycarboxylic acid is contacted with clothing or a textile to provide a benefit, such as disinfecting, bleaching, destaining, deodorizing and/or a combination thereof. The peroxycarboxylic acid may be used in a variety of laundry care products including, but not limited to, laundry or textile pre-wash treatments, laundry detergents or additives, stain removers, bleaching compositions, deodorizing compositions, and rinsing agents. In one embodiment, the present process to produce a peroxycarboxylic acid for a target surface is conducted in situ.

In the context of laundry care applications, the term "contacting an article of clothing or textile" means that the article of clothing or textile is exposed to a formulation disclosed herein. To this end, there are a number of formats the formulation may be used to treat articles of clothing or textiles including, but not limited to, liquid, solids, gel, paste, bars, tablets, spray, foam, powder, or granules and can be delivered via hand dosing, unit dosing, dosing from a substrate, spraying and automatic dosing from a laundry washing or drying machine. Granular compositions can also be in compact form; liquid compositions can also be in a concentrated form.

When the formulations disclosed herein are used in a laundry washing machine, the formulation can further contain components typical to laundry detergents. For example, typical components included, but are not limited to, surfactants, bleaching agents, bleach activators, additional enzymes, suds suppressors, dispersants, lime-soap dispersants, soil suspension and anti-redeposition agents, softening agents, corrosion inhibitors, tarnish inhibitors, germicides, pH adjusting agents, non-builder alkalinity sources, chelating agents, organic and/or inorganic fillers, solvents, hydrotropes, optical brighteners, dyes, and perfumes. For example, a liquid laundry detergent was used in Example 6 comprising 15-30% anionic and non-ionic surfactants, 5-15% soap, and <5% polycarboxylates, perfume, phosphonates, optical brighteners. In a further example, a solid laundry detergent formulation was used in Example 11 generally comprising surfactants (sodium dodecylbenzenesulfonate, C12-15 Pareth-5, C12-15 Pareth-7, sodium stearate, and stearic acid), builders (sodium carbonate, zeolite, sodium silicate, and citric acid), binders (cellulose, PEG-75, dextrin, and sucrose), bulking agents (sodium sulfate, sodium chloride, sodium bicarbonate, and calcium carbonate), structurants (sodium acrylic Acid/MA copolymer, and sodium polyacrylate), sequestrants (tetrasodium etidronate and calcium sodium EDTMP), optical brighteners (disodium anilinomorpholinotriazinylaminostilbenesulfonate), stabilizing agents, anti-redeposition agents, antifoaming agents, and softness extenders.

The formulations disclosed herein can also be used as detergent additive products in solid or liquid form. Such additive products are intended to supplement or boost the performance of conventional detergent compositions and can be added at any stage of the cleaning process.

In connection with the present systems and methods for laundry care where the peracid is generated for one or more of bleaching, stain removal, and odor reduction, the concentration of peracid generated (e.g., peracetic acid) by the perhydrolysis of at least one carboxylic acid ester may be at least about 2 ppm, preferably at least 20 ppm, preferably at least 100 ppm, and more preferably at least about 200 ppm peracid. In connection with the present systems and methods for laundry care where the peracid is generated for disinfection or sanitization, the concentration of peracid generated (e.g., peracetic acid) by the perhydrolysis of at least one carboxylic acid ester may be at least about 2 ppm, more preferably at least 20 ppm, more preferably at least 200 ppm, more preferably at least 500 ppm, more preferably at least 700 ppm, more preferably at least about 1000 ppm peracid, most preferably at least 2000 ppm peracid within 10 minutes, preferably within 5 minutes, and most preferably within 1 minute of initiating the perhydrolysis reaction. The product formulation comprising the peracid may be optionally diluted with water, or a solution predominantly comprised of water, to produce a formulation with the desired lower concentration of peracid. In one aspect of the present methods and systems, the reaction time required to produce the desired concentration of peracid is not greater than about two hours, preferably not greater than about 30 minutes, more preferably not greater than about 10 minutes, even more preferably not greater than about 5 minutes, and most preferably in about 1 minute or less.

The temperature of the reaction is chosen to control both the reaction rate and the stability of the enzyme catalyst activity. The temperature of the reaction may range from just above the freezing point of the aqueous reaction formulation (approximately 0° C.) to about 85° C., with a preferred range of reaction temperature of from about 5° C. to about 75° C.

The pH of the aqueous reaction formulation while enzymatically producing peroxycarboxylic acid is maintained at a pH ranging from about 5.0 to about 10.0, preferably about 6.5 to about 8.5, and yet even more preferably about 6.5 to about 7.5. In one embodiment, the pH of the aqueous reaction formulation ranges from about 6.5 to about 8.5 for at least 30 minutes after combining the reaction components. The pH of the aqueous reaction formulation may be adjusted or controlled by the addition or incorporation of a suitable buffer, including, but not limited to, phosphate, pyrophosphate, bicarbonate, acetate, or citrate. In one embodiment, the buffer is selected from a phosphate buffer, a bicarbonate buffer, or a buffer formed by the combination of hard ward (tap water to simulate laundry care applications) and percarbonate (from sodium percarbonate used to generate hydrogen peroxide). The concentration of buffer, when employed, is typically from 0.1 mM to 1.0 M, preferably from 1 mM to 300 mM, most preferably from 10 mM to 100 mM. In another aspect of the present invention, no buffer is added to the reaction mixture while enzymatically producing peroxycarboxylic acid.

In yet another aspect, the enzymatic perhydrolysis aqueous reaction formulation may contain an organic solvent that acts as a dispersant to enhance the rate of dissolution of the carboxylic acid ester in the aqueous reaction formulation. Such solvents include, but are not limited to, propylene glycol methyl ether, acetone, cyclohexanone, diethylene glycol butyl ether, tripropylene glycol methyl ether, diethylene glycol methyl ether, propylene glycol butyl ether, dipropylene glycol methyl ether, cyclohexanol, benzyl alcohol, isopropanol, ethanol, propylene glycol, and mixtures thereof.

In another aspect, the enzymatic perhydrolysis product may contain additional components that provide desirable functionality. These additional components include, but are not limited to, buffers, detergent builders, thickening agents, emulsifiers, surfactants, wetting agents, corrosion inhibitors (e.g., benzotriazole), enzyme stabilizers, and peroxide stabilizers (e.g., metal ion chelating agents). Many of the additional components are well known in the detergent industry (see, for example, U.S. Pat. No. 5,932,532; hereby incorporated by reference). Examples of emulsifiers include, but are not limited to, polyvinyl alcohol or polyvinylpyrrolidone. Examples of thickening agents include, but are not limited to, LAPONITE® RD, corn starch, PVP, CARBOWAX®, CARBOPOL®, CABOSIL®, polysorbate 20, PVA, and lecithin. Examples of buffering systems include, but are not limited to, sodium phosphate monobasic/sodium phosphate dibasic; sulfamic acid/triethanolamine; citric acid/triethanolamine; tartaric acid/triethanolamine; succinic acid/triethanolamine; and acetic acid/triethanolamine. Examples of surfactants include, but are not limited to, a) non-ionic surfactants such as block copolymers of ethylene oxide or propylene oxide, ethoxylated or propoxylated linear and branched primary and secondary alcohols, and aliphatic phosphine oxides b) cationic surfactants such as quaternary ammonium compounds, particularly quaternary ammonium compounds having a C8-C20 alkyl group bound to a nitrogen atom additionally bound to three C1-C2 alkyl groups, c) anionic surfactants such as alkane carboxylic acids (e.g., C8-C20 fatty acids), alkyl phosphonates, alkane sulfonates (e.g., sodium dodecylsulphate "SDS") or linear or branched alkyl benzene sulfonates, alkene sulfonates and d) amphoteric and zwitterionic surfactants such as aminocarboxylic acids, aminodicarboxylic acids, alkybetaines, and mixtures thereof. Additional components may include fragrances, dyes, stabilizers of hydrogen peroxide (e.g., metal chelators such as 1-hydroxyethylidene-1,1-diphosphonic acid (DEQUEST® 2010, Solutia Inc., St. Louis, Mo.) and ethylenediaminetetraacetic acid (EDTA)), TURPINAL® SL, DEQUEST® 0520, DEQUEST® 0531, stabilizers of enzyme activity (e.g., polyethylene glycol (PEG)), and detergent builders.

In another aspect, the enzymatic perhydrolysis product may be pre-mixed to generate the desired concentration of peroxycarboxylic acid prior to contacting the surface or inanimate object to be disinfected.

In another aspect, the enzymatic perhydrolysis product is not pre-mixed to generate the desired concentration of peroxycarboxylic acid prior to contacting the surface or inanimate object to be disinfected, but instead, the components of the aqueous reaction formulation that generate the desired concentration of peroxycarboxylic acid are contacted with the surface or inanimate object to be disinfected and/or bleached or destained, generating the desired concentration of peroxycarboxylic acid. In some embodiments, the components of the aqueous reaction formulation combine or mix at the locus. In some embodiments, the reaction components are delivered or applied to the locus and subsequently mix or combine to generate the desired concentration of peroxycarboxylic acid.

Production of Peroxycarboxylic Acids Using a Perhydrolase Catalyst

The peroxycarboxylic acids, once produced, are quite reactive and may decrease in concentration over extended periods of time, depending on variables that include, but are not limited to, temperature and pH. As such, it may be desirable to keep the various reaction components separated, especially for liquid formulations. In one aspect, the hydrogen peroxide source is separate from either the substrate or the perhydrolase catalyst, preferably from both. This can be accomplished using a variety of techniques including, but not limited to, the use of multicompartment chambered dispensers (U.S. Pat. No. 4,585,150) and at the time of use physically combining the perhydrolase catalyst with a source of peroxygen (such as hydrogen peroxide) and the present substrates to initiate the aqueous enzymatic perhydrolysis reaction. The perhydrolase catalyst may optionally be immobilized within the body of reaction chamber or separated (e.g., filtered, etc.) from the reaction product comprising the peroxycarboxylic acid prior to contacting the surface and/or object targeted for treatment. The perhydrolase catalyst may be in a liquid matrix or in a solid form (e.g., powder or tablet) or embedded within a solid matrix that is subsequently mixed with the substrates to initiate the enzymatic perhydrolysis reaction. In a further aspect, the perhydrolase catalyst may be contained within a dissolvable or porous pouch that may be added to the aqueous substrate matrix to initiate enzymatic perhydrolysis. In yet a further aspect, the perhydrolase catalyst may comprise the contents contained within a separate compartment of a dissolvable or porous pouch that has at least one additional compartment for the containment contents comprising the ester substrate and/or source of peroxide. In an additional further aspect, a powder comprising the enzyme catalyst is suspended in the substrate (e.g., triacetin), and at time of use is mixed with a source of peroxygen in water.

Method for Determining the Concentration of Peroxycarboxylic Acid and Hydrogen Peroxide.

A variety of analytical methods can be used in the present method to analyze the reactants and products including, but not limited to, titration, high performance liquid chromatography (HPLC), gas chromatography (GC), mass spectroscopy (MS), capillary electrophoresis (CE), the analytical procedure described by U. Karst et al. (*Anal. Chem.,* 69(17): 3623-3627 (1997)), and the 2,2'-azino-bis(3-ethylbenzothazoline)-6-sulfonate (ABTS) assay (S. Minning, et al., *Analytica Chimica Acta* 378:293-298 (1999) and WO 2004/058961 A1) as described in U.S. Pat. No. 7,951,566.

Determination of Minimum Biocidal Concentration of Peroxycarboxylic Acids

The method described by J. Gabrielson et al. (*J. Microbiol. Methods* 50: 63-73 (2002)) can be employed for determination of the Minimum Biocidal Concentration (MBC) of peroxycarboxylic acids, or of hydrogen peroxide and enzyme substrates. The assay method is based on XTT reduction inhibition, where XTT (2,3-bis[2-methoxy-4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to, viable plate counts, direct microscopic counts, dry weight, turbidity measurements, absorbance, and bioluminescence (see, for example Brock, Semour S., *Disinfection, Sterilization, and Preservation,* 5th edition, Lippincott Williams & Wilkins, Philadelphia, Pa., USA; 2001).

Uses of Enzymatically Prepared Peroxycarboxylic Acid Compositions

The enzyme catalyst-generated peroxycarboxylic acid produced according to the present method can be used in a variety of hard surface/inanimate object applications for reduction of concentrations of biological contaminants, such as decontamination of medical instruments (e.g., endoscopes), textiles (such as garments and carpets), food preparation surfaces, food storage and food-packaging equipment, materials used for the packaging of food products, chicken hatcheries and grow-out facilities, animal enclosures, and spent process waters that have microbial and/or virucidal activity. The enzyme-generated peroxycarboxylic acids may be used in formulations designed to inactivate prions (e.g., certain proteases) to additionally provide biocidal activity (see U.S. Pat. No. 7,550,420 to DiCosimo et al.).

In one aspect, the peroxycarboxylic acid composition is useful as a disinfecting agent for non-autoclavable medical instruments and food packaging equipment. As the peroxycarboxylic acid-containing formulation may be prepared using GRAS or food-grade components (enzyme, enzyme substrate, hydrogen peroxide, and buffer), the enzyme-generated peroxycarboxylic acid may also be used for decontamination of animal carcasses, meat, fruits and vegetables, or for decontamination of prepared foods. The enzyme-generated peroxycarboxylic acid may be incorporated into a product whose final form is a powder, liquid, gel, film, solid or aerosol. The enzyme-generated peroxycarboxylic acid may be diluted to a concentration that still provides an efficacious decontamination.

The compositions comprising an efficacious concentration of peroxycarboxylic acid can be used to disinfect surfaces and/or objects contaminated (or suspected of being contaminated) with biological contaminants, such as pathogenic microbial contaminants, by contacting the surface or object with the products produced by the present processes. As used herein, "contacting" refers to placing a disinfecting composition comprising an effective concentration of peroxycarboxylic acid in contact with the surface or inanimate object suspected of contamination with a biological contaminant for a period of time sufficient to clean and disinfect. Contacting includes spraying, treating, immersing, flushing, pouring on or in, mixing, combining, painting, coating, applying, affixing to and otherwise communicating a peroxycarboxylic acid solution or composition comprising an efficacious concentration of peroxycarboxylic acid, or a solution or composition that forms an efficacious concentration of peroxycarboxylic acid, with the surface or inanimate object suspected of being contaminated with a concentration of a biological contaminant. The disinfectant compositions may be combined with a cleaning composition to provide both cleaning and disinfection. Alternatively, a cleaning agent (e.g., a surfactant or detergent) may be incorporated into the formulation to provide both cleaning and disinfection in a single composition.

The compositions comprising an efficacious concentration of peroxycarboxylic acid can also contain at least one additional antimicrobial agent, combinations of prion-degrading proteases, a virucide, a sporicide, or a biocide. Combinations of these agents with the peroxycarboxylic acid produced by the claimed processes can provide for increased and/or synergistic effects when used to clean and disinfect surfaces and/or objects contaminated (or suspected of being contaminated) with biological contaminants. Suitable antimicrobial agents include carboxylic esters (e.g., p-hydroxy alkyl benzoates and alkyl cinnamates), sulfonic acids (e.g., dodecylbenzene sulfonic acid), iodo-compounds or active halogen compounds (e.g., elemental halogens, halogen oxides (e.g., NaOCl, HOC/, HOBr, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$-$C_6$ alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection. Effective amounts of antimicrobial agents include about 0.001 wt % to about 60 wt % antimicrobial agent, about 0.01 wt % to about 15 wt % antimicrobial agent, or about 0.08 wt % to about 2.5 wt % antimicrobial agent.

In one aspect, the peroxycarboxylic acids formed by the process can be used to reduce the concentration of viable biological contaminants (such as a microbial population) when applied on and/or at a locus. As used herein, a "locus" comprises part or all of a target surface suitable for disinfecting or bleaching. Target surfaces include all surfaces that can potentially be contaminated with biological contaminants. Non-limiting examples include equipment surfaces found in the food or beverage industry (such as tanks, conveyors, floors, drains, coolers, freezers, equipment surfaces, walls, valves, belts, pipes, drains, joints, crevasses, combinations thereof, and the like); building surfaces (such as walls, floors and windows); non-food-industry related pipes and drains, including water treatment facilities, pools and spas, and fermentation tanks; hospital or veterinary surfaces (such as walls, floors, beds, equipment (such as endoscopes), clothing worn in hospital/veterinary or other healthcare settings, including clothing, scrubs, shoes, and other hospital or veterinary surfaces); restaurant surfaces; bathroom surfaces; toilets; clothes and shoes; surfaces of barns or stables for livestock, such as poultry, cattle, dairy cows, goats, horses and pigs; hatcheries for poultry or for shrimp; and pharmaceutical or biopharmaceutical surfaces (e.g., pharmaceutical or biopharmaceutical manufacturing equipment, pharmaceutical or biopharmaceutical ingredients, pharmaceutical or biopharmaceutical excipients). Additional hard surfaces include food products, such as beef, poultry, pork, vegetables, fruits, seafood, combinations thereof, and the like. The locus can also include water absorbent materials such as infected linens or other textiles. The locus also includes harvested plants or plant products including seeds, corms, tubers, fruit, and vegetables, growing plants, and especially crop growing plants, including cereals, leaf vegetables and salad crops, root vegetables, legumes, berried fruits, citrus fruits and hard fruits.

Non-limiting examples of hard surface materials are metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth)acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon). Additional surfaces include brick, tile, ceramic, porcelain, wood, wood pulp, paper, vinyl, linoleum, and carpet.

The peroxycarboxylic acids formed by the present process may be used to provide a benefit to an article of clothing or a textile including, but not limited to disinfecting, sanitizing, bleaching, destaining, and deodorizing. The peroxycarboxylic acids formed by the present process may be used in any number of laundry care products including, but not limited to textile pre-wash treatments, laundry detergents, laundry detergents or additives, stain removers, bleaching compositions, deodorizing compositions, and rinsing agents, to name a few.

The peroxycarboxylic acids formed by the present process can be used in one or more steps of the wood pulp or paper pulp bleaching/delignification process, particularly where peracetic acid is used (for example, see EP1040222 B1 and U.S. Pat. No. 5,552,018 to Devenyns, J.).

Recombinant Microbial Expression

The genes and gene products of the instant sequences may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The perhydrolase may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to, bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, bacterial host strains include *Escherichia, Bacillus*, and *Pseudomonas*. In a preferred embodiment, the bacterial host cell is *Escherichia coli*.

Industrial Production

A variety of culture methodologies may be applied to produce the perhydrolase catalyst Large-scale production of a specific gene product over expressed from a recombinant microbial host may be produced by batch, fed-batch or continuous culture methodologies. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem. Biotechnol.,* 36:227 (1992).

In one embodiment, commercial production of the desired perhydrolase catalyst is accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Recovery of the desired perhydrolase catalysts from a batch or fed-batch fermentation, or continuous culture may be accomplished by any of the methods that are known to those skilled in the art. For example, when the enzyme catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired enzyme catalyst. The cell extract may optionally be filtered through an appropriate filter aid such as celite or silica to remove cell debris prior to a heat-treatment step to precipitate undesired protein from the enzyme catalyst solution. The solution containing the desired enzyme catalyst may then be separated from the precipitated cell debris and protein produced during the heat-treatment step by membrane filtration or centrifugation, and the resulting partially-purified enzyme catalyst solution concentrated by additional membrane filtration, then optionally mixed with an appropriate excipient (for example, maltodextrin, trehalose, sucrose, lactose, sorbitol, mannitol, phosphate buffer, citrate buffer, or mixtures thereof) and spray-dried to produce a solid powder comprising the desired enzyme catalyst. Alternatively, the resulting partially-purified enzyme catalyst solution prepared as described above may be optionally concentrated by additional membrane filtration, and the partially-purified enzyme catalyst solution or resulting enzyme concentrate is then optionally mixed with one or more stabilizing agents (e.g., glycerol, sorbitol, propylene glycol, 1,3-propanediol, polyols, polymeric polyols, polyvinylalcohol or mixtures thereof), one or more salts (e.g., sodium chloride, sodium sulfate, potassium chloride, potassium sulfate, or mixtures thereof), and one or more biocides, and maintained as an aqueous solution until used.

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

GENERAL METHODS

The following examples are provided to demonstrate different embodiments. It should be appreciated by those of skill in the art that the techniques disclosed in the examples which follow represent techniques discovered by the inventor to function well in the practice of the methods disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the presently disclosed methods.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma-Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "μL" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "μg" means microgram(s), "ng" means nanogram(s), "g" means gravity, "HPLC" means high performance liquid chromatography, "dd $H_2O$" means distilled and deionized water, "dcw" means dry cell weight, "ATCC" or "ATCC®" means the American Type Culture Collection (Manassas, Va.), "U" means unit(s) of perhydrolase activity, "rpm" means revolution(s) per minute, and "EDTA" means ethylenediaminetetraacetic acid.

EXAMPLE 1

Construction of a Random Mutagenesis Library of *Thermotoga maritima* Acetyl Xylan Esterase C277T Variant The coding sequence of a *Thermotoga maritima* acetyl xylan esterase (GENBANK® accession # NP_227893.1) was synthesized using codons optimized for expression in *E. coli* (DNA 2.0, Menlo Park, Calif.) and cloned into pUC19 between Pst1 and Xba1 to create the plasmid known as pSW202 (U.S. Patent Application Publication No. 2008-0176299). The codon-optimized sequence is provided as SEQ ID NO: 1 encoding the wild-type *Thermotoga maritime* acetyl xylan esterase provided as SEQ ID NO: 2.

A codon change was made in the gene using primer pairs identified as SEQ ID NO: 3 and SEQ ID NO: 4, and the QUIKCHANGE® site-directed mutagenesis kit (Stratagene, La Jolla, Calif.), according to the manufacturer's instructions, resulting in the amino acid change C277T (SEQ ID NO: 5), to create the plasmid known as pSW202/C277T (SEQ ID NO: 6). Plasmid pSW202/C277T served as a template for error-prone PCR using primers identified as SEQ ID NO: 7 and SEQ ID NO: 8, and the GENEMORPH® II random mutagenesis kit (Stratagene), according to the manufacturer's recommendations. The resulting PCR product was digested with Pst1 and Xba1 and ligated with pUC19 also digested with Pst1 and Xba1. *E. coli* KLP18 (see U.S. Patent Application Publication No. 2008-0176299) was transformed with the ligation mixture and plated onto LB plates supplemented with 0.1 mg ampicillin/mL. Nucleotide sequencing of a random sample indicated a mutation frequency of 2-8 changes per PCR product.

EXAMPLE 2

Screening of *Thermotoga maritime* Error-Prone PCR Library for Increased Enzyme Activity Colonies were picked (automated) and placed into 96-well "master plates" containing 0.1 mL LB media supplemented with 0.1 mg ampicillin/mL and grown 16-18 h at 37° C. and 80% humidity. From each well of the master plates, 0.003 mL of culture was transferred to 96-well "induction plates" containing 0.3 mL LB media supplemented with 0.1 mg ampicillin/mL and 0.5 mM IPTG, which were incubated for 16-18 h with shaking at 37° C. and 80% humidity. Separately, 0.1 mL of 50% glycerol was added to each well of the master plates, which were stored at −80° C. as stocks. From each well of the induction plates, 0.01 mL of culture was transferred to 96-well "lysis plates" containing 0.09 mL of 56 mg/mL CELLYTIC™ Express (Sigma Aldrich, St. Louis, Mo.), which were incubated for 30 minutes at 30° C. From each well of the lysis plates, 0.01 mL of material was transferred to 96-well "assay plates" containing 0.045 mL "assay solution part 1" (10 mM triacetin, 50 mM potassium phosphate buffer, pH 7.0). To each well of the assay plates was then added 0.045 mL of "assay solution part 2" (20 mM hydrogen peroxide). Plates were gently mixed and incubated for 2 minutes at 30° C. To each well of the assay plate was added 0.1 mL of "stop buffer" (100 mM o-phenylenediamine and 500 mM sodium dihydrogen phosphate, pH 2.0). The plates were incubated for 30 minutes at 30° C., after which absorbance at 458 nm was read. *T. maritima* WT (codon optimized gene (SEQ ID NO: 1) encoding the wild type enzyme (SEQ ID NO: 2)) and *T. maritima* C277T (SEQ ID NO: 5) were incorporated into each plate as controls. Screening approximately 7000 colonies resulted in the identification of numerous "hits" demonstrating activity significantly greater than *T. maritima* C277T (SEQ ID NO: 5). Nucleotide sequencing was used to determine the amino acid changes in the perhydrolase enzyme of these hits (Table 1).

TABLE 1

*T. maritima* perhydrolase variants having perhydrolytic activity greater than variant C277T identified in primary screen.

| variant ID | # of amino acid changes | amino acid changes relative to *T. maritima* WT sequence | | | | | | nucleic acid SEQ ID | amino acid SEQ ID |
|---|---|---|---|---|---|---|---|---|---|
| 006D11 | 5 | W28R | P84S | S201G | E243D | C277T | | 9 | 10 |
| 006F12 | 3 | R261S | I264F | C277T | | | | 11 | 12 |
| 006D10 | 4 | W28C | L32P | D151E | C277T | | | 13 | 14 |
| 006B12 | 3 | W28C | F104S | C277T | | | | 15 | 16 |
| 006E11 | 2 | V183D | C277T | | | | | 17 | 18 |
| 006H5 | 2 | C277T | L318P | | | | | 19 | 20 |
| 006B5 | 3 | P265L | C277T | I297N | | | | 21 | 22 |
| 006F3 | 6 | P16L | F38S | T53N | R159C | V183D | C277T | 23 | 24 |
| 006G10 | 4 | R15H | Q176H | L208Q | C277T | | | 25 | 26 |
| 006F1 | 2 | L32P | C277T | | | | | 27 | 28 |
| 006A10 | 2 | F268S | C277T | | | | | 29 | 30 |
| 006G6 | 4 | E29G | S62P | F174L | C277T | | | 31 | 32 |
| 006E10 | 3 | R218C | C277T | F317L | | | | 33 | 34 |
| 006D9 | 2 | C277T | R296P | | | | | 35 | 36 |
| 006F7 | 3 | E9K | G255C | C277T | | | | 37 | 38 |
| 006E12 | 4 | H227L | T233A | C277T | A290V | | | 39 | 40 |
| 006F8 | 3 | Q67R | K82E | C277T | | | | 41 | 42 |
| 006G8 | 3 | F247L | C277T | V282D | | | | 43 | 44 |
| 006G11 | 2 | D254G | C277T | | | | | 45 | 46 |
| 006E9 | 3 | E17V | R261H | C277T | | | | 47 | 48 |
| 006F10 | 5 | F24L | T31S | E48V | C277T | K316E | | 49 | 50 |
| 006F5 | 5 | V43G | G63C | H100L | C277T | A284V | | 51 | 52 |
| 006E7 | 4 | F258Y | E294G | C277T | L318P | | | 53 | 54 |
| 006G12 | 2 | F161L | C277T | | | | | 55 | 56 |
| 006H01 | 2 | F253S | C277T | | | | | 57 | 58 |
| 006G2 | 2 | F24I | C277T | | | | | 59 | 60 |
| 006F6 | 2 | A206T | C277T | | | | | 61 | 62 |
| 006C10 | 2 | E55K | C277T | | | | | 63 | 64 |
| 006F9 | 2 | Q67R | C277T | | | | | 65 | 66 |
| control | 1 | C277T | | | | | | | 5 |

EXAMPLE 3

Construction of Site Saturation Libraries of *Thermotoga maritima* Acetyl Xylan Esterase C277S Variants Using the codon-optimized *Thermotoga maritima* gene encoding acetyl xylan esterase described in Example 1 (SEQ ID NO: 1 encoding SEQ ID NO: 2), a codon change was made in the gene using primer pairs identified as SEQ ID NO: 67 and SEQ ID NO: 68, and the QUIKCHANGE® site-directed mutagenesis kit (Stratagene, La Jolla, Calif.), according to the manufacturer's instructions, resulting in a gene containing the amino acid change C277S (SEQ ID NO: 69), to create the plasmid known as pSW202/C277S (SEQ ID NO: 70). Based on previous screening results of random mutagenesis libraries, 6 residues (S35, K77, L125, A266, N275 and N302) were selected for saturation mutagenesis. Six site saturation mini-libraries (approx 500 members each) were constructed using degenerate primers pairs (SEQ ID NOs: 71-82) and the QUIKCHANGE® site-directed mutagenesis kit (Stratagene, La Jolla, Calif.).

EXAMPLE 4

Screening of *Thermotoga maritima* Site Saturation Mutagenesis Library for Increased Enzyme Activity Colonies were picked (automated) and placed into 96-well "master plates" containing 0.1 mL LB media supplemented with 0.1 mg ampicillin/mL and grown 16-18 h at 37° C. and 80% humidity. From each well of the master plates, 0.003 mL of culture was transferred to 96-well "induction plates" containing 0.3 mL LB media supplemented with 0.1 mg ampicillin/mL and 0.5 mM IPTG, which were incubated for 16-18 h with shaking at 37° C. and 80% humidity. Separately, 0.1 mL of 50% glycerol was added to each well of the master plates, which were stored at −80° C. as stocks. From each well of the induction plates, 0.01 mL of culture was transferred to 96-well "lysis plates" containing 0.09 mL of 56 mg/mL CELLYTIC™ Express (Sigma Aldrich, St. Louis, Mo.), which were incubated for 30 minutes at 30° C. From each well of the lysis plates, 0.01 mL of material was transferred to 96-well "assay plates" containing 0.045 mL "assay solution part 1" (10 mM triacetin, 50 mM potassium phosphate buffer, pH 7.0). To each well of the assay plates was then added 0.045 mL of "assay solution part 2" (20 mM hydrogen peroxide). Plates were gently mixed and incubated for 2 minutes at 30° C. To each well of the assay plate was added 0.1 mL of "stop buffer" (100 mM o-phenylenediamine and 500 mM sodium dihydrogen phosphate, pH 2.0). The plates were incubated for 30 minutes at 30° C., after which absorbance at 458 nm was read. *T. maritima* WT (codon optimized gene (SEQ ID NO: 1) encoding the wild type enzyme (SEQ ID NO: 2)) and *T. maritima* C277S (SEQ ID NO: 69) were incorporated into each plate as controls. Screening approximately 3000 colonies resulted in the identification of numerous "hits" demonstrating activity significantly greater than *T. maritime* C277S (SEQ ID NO: 69). Nucleotide sequencing was used to determine the amino acid changes in the perhydrolase enzyme of these hits (Table 2).

TABLE 2

*T. maritima* perhydrolase variants having perhydrolytic activity greater than variant C277S.

| ID | mutations relative to WT | | nucleic acid SEQ ID | amino acid SEQ ID |
|---|---|---|---|---|
| 873C8 | S35R | C277S | 83 | 84 |
| 873D7 | S35K | C277S | 85 | 86 |
| 873D3 | S35E | C277S | 87 | 88 |
| 873C9 | S35N | C277S | 89 | 90 |
| 873H5 | K77A | C277S | 91 | 92 |
| 873G12 | K77V | C277S | 93 | 94 |
| 873H1 | K77D | C277S | 95 | 96 |
| 873A4 | L125M | C277S | 97 | 98 |
| 873A9 | L125R | C277S | 99 | 100 |
| 873B4 | A266P | C277S | 101 | 102 |
| 873B2 | A266D | C277S | 103 | 104 |
| 873G7 | A266I | C277S | 105 | 106 |
| 873C3 | A266E | C277S | 107 | 108 |
| 873B3 | A266N | C277S | 109 | 110 |
| 873B12 | A266R | C277S | 111 | 112 |
| 873G3 | A266Q | C277S | 113 | 114 |
| 873E2 | A266V | C277S | 115 | 116 |

EXAMPLE 5

Production of Variant *Thermotoga maritima* Perhydrolases

Variant strains identified in screens were grown in LB media at 37° C. with shaking up to $OD_{600\ nm}$=0.4-0.5, at which time IPTG was added to a final concentration of 1 mM, and incubation continued for 2-3 h. Cells were harvested by centrifugation and SDS-PAGE was performed to confirm expression of the perhydrolase enzyme at 20-40% of total soluble protein.

EXAMPLE 6

Preparation of Heat-treated Cell Extracts Containing Semi-Purified Variant *Thermotoga maritima* Perhydrolases Cell cultures (prepared as described in Example 5) were harvested by centrifugation at 5,000×g for 15 minutes then resuspended (20% w/v) in 50 mM phosphate buffer pH 7.0 supplemented with 1.0 mM DTT. Resuspended cells were passed through a French pressure cell twice to ensure >95% cell lysis. Lysed cells were centrifuged for 30 minutes at 12,000×g, and the supernatant was heated at 75° C. for 20 minutes, followed by quenching in an ice bath for 2 minutes. Precipitated protein was removed by centrifugation for 10 minutes at 11,000×g. The resulting heat-treated extract supernatants were analyzed for mg total soluble protein/mL using BCA assay, and stored frozen at −80° C. Analysis of a first set of heat-treated extract supernatants produced by this method using PAGE indicated that the perhydrolase variant comprised approximately 85-90% of the total soluble protein in the heat-treated extract supernatant. Analysis of a second set of heat-treated extract supernatants produced by this method using PAGE indicated that the perhydrolase variant comprised approximately 65-70% of the total soluble protein in the heat-treated extract supernatant. In the following Examples, the individual Tables contain data obtained using a single set of heat-treated extract supernatants that contained the same concentration of perhydrolase variant as a percentage of total soluble protein.

EXAMPLE 7

Comparison of Perhydrolase Variants Vs. *Thermotoga maritima* C277T Variant Perhydrolase Using 2 Mm Triacetin and 10 Mm $H_2O_2$ in Sodium Bicarbonate Buffer (10 mM, pH 6.5) at 20° C.

Reactions (100 mL total volume) were run at 20° C. in sodium bicarbonate buffer (10 mM, pH 6.5) containing triacetin (2 mM), hydrogen peroxide (10 mM) and 2.0 μg/mL of heat-treated extract total soluble protein containing an error-prone PCR (epPCR)-generated variant perhydrolase prepared as described in Example 6. Reactions were stirred for only the first 45 seconds of reaction to initially mix the reactants and enzyme.

A comparative reaction was also run under identical conditions to that described immediately above using 2.0 μg/mL of heat-treated extract total soluble protein isolated from *E. coli* KLP18/pSW228/C277T (expressing *Thermotoga maritima* C277T perhydrolase variant (SEQ ID NO: 5)), where the heat-treated extract supernatant was prepared according to the procedure of Example 6, and where this heat-treated extract supernatant contained the same concentration of *Thermotoga maritime* C277T perhydrolase variant (SEQ ID NO: 5) as a percentage of total soluble protein as was present in the heat-treated extract total soluble protein containing an error-prone PCR (epPCR)-generated variant perhydrolase.

Reaction samples were analyzed for the amount of peracetic acid (PAA) produced at 5 minutes and 20 minutes after combining the reaction components using a modification of the method described by Karst et al., supra. A sample (0.200 mL) of the reaction mixture was removed at a predetermined time and immediately mixed with 0.200 mL of 50 mM phosphoric acid in water to terminate the reaction by adjusting the pH of the diluted sample to less than pH 4. The resulting solution was filtered using an ULTRAFREE® MC-filter unit (30,000 Normal Molecular Weight Limit (NMWL), Millipore Corp., Billerica, Mass.; cat #UFC3LKT 00) by centrifugation for 2 min at 12,000 rpm. An aliquot (0.100 mL) of the resulting filtrate was transferred to a 1.5-mL screw cap HPLC vial (Agilent Technologies, Palo Alto, Calif.; #5182-0715) containing 0.300 mL of deionized water, then 0.100 mL of 20 mM MTS (methyl-p-tolyl sulfide) in acetonitrile was added, the vial capped, and the contents briefly mixed prior to a 10 min incubation at ca. 25° C. in the absence of light. To the vial was then added 0.400 mL of acetonitrile and 0.100 mL of a solution of triphenylphosphine (TPP, 120 mM) in acetonitrile, the vial re-capped, and the resulting solution mixed and incubated at ca. 25° C. for 30 min in the absence of light. To the vial was then added 0.100 mL of 2.5 mM N,N-diethyl-m-toluamide (DEET; HPLC external standard) and the resulting solution analyzed by HPLC for MTSO (methyl-p-tolyl sulfoxide), the stoichiometric oxidation product produced by reaction of MTS with peracetic acid. A control reaction was run in the absence of added extract protein or triacetin to determine the rate of oxidation of MTS in the assay mixture by hydrogen peroxide, for correction of the rate of peracetic acid production for background MTS oxidation. HPLC method: Supelco Discovery C8 column (10-cm×4.0-mm, 5 μm) (catalog #569422-U) with Supelco Supelguard Discovery C8 precolumn (Sigma-Aldrich; catalog #59590-U); 10 microliter injection volume; gradient method with $CH_3CN$ (Sigma-Aldrich; catalog #270717) and deionized water at 1.0 mL/min and ambient temperature (Table 3).

TABLE 3

HPLC Gradient for analysis of peracetic acid.

| Time (min:sec) | (% $CH_3CN$) |
|---|---|
| 0:00 | 40 |
| 3:00 | 40 |
| 3:10 | 100 |
| 4:00 | 100 |
| 4:10 | 40 |
| 7:00 (stop) | 40 |

Several variants were identified that produced a higher concentration of PAA at one or both time points when compared to the *T. maritima* C277T variant perhydrolase (Published U.S. Patent Application No. 2010-0087529 to DiCosimo et al., SEQ ID NO: 5). As shown in Tables 4 and 5, variants 006B12 (W28C1F104S/C277T; SEQ ID NO: 16), 006F12 (R261S/I1264F/C277T; SEQ ID NO: 12), and 006D10 (W28C/L32P/D151E/C277T; SEQ ID NO: 14) were able to produce more peracetic acid when compared to the *T. maritima* C277T perhydrolase (SEQ ID NO: 5) under the specified conditions (either with or without added liquid detergent at pH 6.5).

TABLE 4

Peracetic acid (PAA) production at 5 minutes and 20 minutes from variants 006B12 vs. *T. maritima* C277T in sodium bicarbonate buffer (10 mM, pH 6.5) at 20° C., 2.0 μg/mL heat-treated extract total soluble protein and 0 mg/mL and 2.0 mg/mL liquid laundry detergent.

| Variant ID | SEQ ID NO: | Samples | Triacetin (mM) | $H_2O_2$ (mM) | Total soluble protein (μg/mL) | Liquid detergent (mg/mL) | Initial pH | PAA @ 5 min. (ppm) | PAA @ 20 min. (ppm) |
|---|---|---|---|---|---|---|---|---|---|
| | | no perhydrolase | 2 | 10 | 0 | 0 | 6.5 | 0.2 | 1.4 |
| Control | 5 | C277T | 2 | 10 | 2.0 | 0 | 6.5 | 51 | 73 |
| Control | 5 | C277T | 2 | 10 | 2.0 | 0 | 6.5 | 46 | 68 |
| 006B12 | 16 | W28C/F104S/C277T | 2 | 10 | 2.0 | 0 | 6.5 | 48 | 63 |
| 006B12 | 16 | W28C/F104S/C277T | 2 | 10 | 2.0 | 0 | 6.5 | 53 | 71 |
| | | no perhydrolase | 2 | 10 | 0 | 2 | 6.5 | 0.7 | 0.7 |
| Control | 5 | C277T | 2 | 10 | 2.0 | 2 | 6.5 | 26 | 45 |
| Control | 5 | C277T | 2 | 10 | 2.0 | 2 | 6.5 | 24 | 44 |
| 006B12 | 16 | W28C/F104S/C277T | 2 | 10 | 2.0 | 2 | 6.5 | 32 | 48 |
| 006B12 | 16 | W28C/F104S/C277T | 2 | 10 | 2.0 | 2 | 6.5 | 36 | 50 |

TABLE 5

Peracetic acid (PAA) production at 5 minutes and 20 minutes from variants 006F12 and 006D10 vs. *T. maritima* C277T in sodium bicarbonate buffer (10 mM, pH 7.2) at 20° C., 2.0 μg/mL heat-treated extract total soluble protein, and 0 mg/mL or 2.0 mg/mL liquid laundry detergent.

| Variant ID | SEQ ID NO: | Samples | Triacetin (mM) | $H_2O_2$ (mM) | Total soluble protein (μg/mL) | Liquid detergent (mg/mL) | Initial pH | PAA @ 5 min. (ppm) | PAA @ 20 min. (ppm) |
|---|---|---|---|---|---|---|---|---|---|
| | | no perhydrolase | 2 | 10 | 0 | 0 | 10 | 0.2 | 1.4 |
| Control | 5 | C277T | 2 | 10 | 2.0 | 0 | 10 | 39 | 70 |
| Control | 5 | C277T | 2 | 10 | 2.0 | 0 | 10 | 38 | 63 |
| 006F12 | 12 | R261S/I264F/C277T | 2 | 10 | 2.0 | 0 | 10 | 51 | 75 |
| 006F12 | 12 | R261S/I264F/C277T | 2 | 10 | 2.0 | 0 | 10 | 49 | 68 |
| 006D10 | 14 | W28C/L32P/D151E/C277T | 2 | 10 | 2.0 | 0 | 10 | 45 | 69 |
| 006D10 | 14 | W28C/L32P/D151E/C277T | 2 | 10 | 2.0 | 0 | 10 | 44 | 61 |
| | | no perhydrolase | 2 | 10 | 0 | 2 | 10 | 0.7 | 0.7 |
| Control | 5 | C277T | 2 | 10 | 2.0 | 2 | 10 | 26 | 45 |
| Control | 5 | C277T | 2 | 10 | 2.0 | 2 | 10 | 22 | 39 |
| 006F12 | 12 | R261S/I264F/C277T | 2 | 10 | 2.0 | 2 | 10 | 31 | 51 |
| 006F12 | 12 | R261S/I264F/C277T | 2 | 10 | 2.0 | 2 | 10 | 27 | 44 |
| 006D10 | 14 | W28C/L32P/D151E/C277T | 2 | 10 | 2.0 | 2 | 10 | 26 | 39 |
| 006D10 | 14 | W28C/L32P/D151E/C277T | 2 | 10 | 2.0 | 2 | 10 | 25 | 38 |

EXAMPLE 8

Comparison of *Thermotoga maritima* Perhydrolase Variants Vs. *Thermotoga maritima* C277T Perhydrolase Under Simulated Laundry Care Application Conditions Five error-prone PCR (epPCR)-generated variant perhydrolases were evaluated for peracetic acid (PAA) production under laundry application conditions (10 mL total volume, 2 mM triacetin (TA), 10 mM $H_2O_2$ from sodium percarbonate in hard water (HW, 400 ppm Ca ion), 2.0 μg/mL of heat-treated extract total soluble protein containing an error-prone PCR (epPCR)-generated variant perhydrolase prepared as described in Example 6) using 0 g/L or 2 g/L of liquid laundry detergent (comprising 15-30% anionic and non-ionic surfactants, 5-15% soap, and <5% polycarboxylates, perfume, phosphonates, optical brighteners) and compared to PAA production using the same concentration of C277T variant perhydrolase (Published U.S. Patent Application No. 2010-0087529 to DiCosimo et al., SEQ ID NO: 5). The results of the various comparisons under simulated laundry care conditions are provided in Tables 6, 7 and 8. Under these reaction conditions, variants 006B12 (W28C/F104S/C277T, SEQ ID NO: 16), 006F12 (R261S/I264F/C277T, SEQ ID NO: 12), 006D10 (W28C/L32P/D151E/C277T, SEQ ID NO: 14), 006E10 (R218C/C277T/F317L, SEQ ID NO: 34) and 006A10 (F268S/C277T, SEQ ID NO: 30) show a measurable improvement in specific activity for peracetic acid production when compared to the *T. maritima* C277T perhydrolase (SEQ ID NO: 5) under the specified conditions (either with or without added liquid detergent at pH 10.0).

TABLE 6

Peracetic acid (PAA) production at 5 minutes and 20 minutes from variant 006B12 vs. *T. maritima* C277T in hard water (HW) (pH 10) at 20° C., 2.0 μg/mL heat-treated extract total soluble protein and 0 mg/mL or 2.0 mg/mL liquid laundry detergent.

| Variant ID | SEQ ID NO: | Samples | Triacetin (mM) | $H_2O_2$[1] (mM) | Total soluble protein (μg/mL) | Liquid detergent (mg/mL) | Initial pH | PAA @ 5 min. (ppm) | PAA @ 20 min. (ppm) |
|---|---|---|---|---|---|---|---|---|---|
| | | no perhydrolase | 2 | 10 | 0 | 0 | 10 | 16 | 45 |
| Control | 5 | C277T | 2 | 10 | 2.0 | 0 | 10 | 74 | 123 |
| Control | 5 | C277T | 2 | 10 | 2.0 | 0 | 10 | 67 | 106 |
| 006B12 | 16 | W28C/F104S/C277T | 2 | 10 | 2.0 | 0 | 10 | 79 | 123 |
| 006B12 | 16 | W28C/F104S/C277T | 2 | 10 | 2.0 | 0 | 10 | 79 | 123 |
| | | no perhydrolase | 2 | 10 | 0 | 2 | 10 | 28 | 27 |
| Control | 5 | C277T | 2 | 10 | 2.0 | 2 | 10 | 51 | — |
| Control | 5 | C277T | 2 | 10 | 2.0 | 2 | 10 | 50 | 89 |
| 006B12 | 16 | W28C/F104S/C277T | 2 | 10 | 2.0 | 2 | 10 | 64 | 96 |
| 006B12 | 16 | W28C/F104S/C277T | 2 | 10 | 2.0 | 2 | 10 | 59 | 86 |

[1]= Hydrogen peroxide generated from sodium percarbonate.

TABLE 7

Peracetic acid (PAA) production at 5 minutes and 20 minutes from variants 006F12 and 006D10 vs. *T. maritima* C277T in hard water (HW) and carbonate buffer (pH 10) at 20° C., 2.0 μg/mL heat-treated extract total soluble protein and 0 mg/mL or 2.0 mg/mL liquid laundry detergent.

| Variant ID | SEQ ID NO: | Samples | Triacetin (mM) | $H_2O_2$[1] (mM) | Total soluble protein (μg/mL) | Liquid detergent (mg/mL) | Initial pH | PAA @ 5 min. (ppm) | PAA @ 20 min. (ppm) |
|---|---|---|---|---|---|---|---|---|---|
| | | no perhydrolase | 2 | 10 | 0 | 0 | 10 | 16 | 45 |
| Control | 5 | C277T | 2 | 10 | 2.0 | 0 | 10 | 55 | 112 |
| Control | 5 | C277T | 2 | 10 | 2.0 | 0 | 10 | 55 | 113 |
| 006F12 | 12 | R261S/I264F/C277T | 2 | 10 | 2.0 | 0 | 10 | 56 | 89 |
| 006F12 | 12 | R261S/I264F/C277T | 2 | 10 | 2.0 | 0 | 10 | 56 | 94 |
| 006D10 | 14 | W28C/L32P/D151E/C277T | 2 | 10 | 2.0 | 0 | 10 | 53 | 87 |
| 006D10 | 14 | W28C/L32P/D151E/C277T | 2 | 10 | 2.0 | 0 | 10 | 54 | 92 |
| | | no perhydrolase | 2 | 10 | 0 | 2 | 10 | 28 | 27 |
| Control | 5 | C277T | 2 | 10 | 2.0 | 2 | 10 | 40 | 79 |
| Control | 5 | C277T | 2 | 10 | 2.0 | 2 | 10 | 39 | 75 |
| 006F12 | 12 | R261S/I264F/C277T | 2 | 10 | 2.0 | 2 | 10 | 56 | 89 |
| 006F12 | 12 | R261S/I264F/C277T | 2 | 10 | 2.0 | 2 | 10 | 56 | 91 |
| 006D10 | 14 | W28C/L32P/D151E/C277T | 2 | 10 | 2.0 | 2 | 10 | 47 | 84 |
| 006D10 | 14 | W28C/L32P/D151E/C277T | 2 | 10 | 2.0 | 2 | 10 | 48 | 83 |

[1]= Hydrogen peroxide generated from sodium percarbonate.

TABLE 8

Peracetic acid (PAA) production at 5 minutes and 20 minutes from variants 006E10 and 006A10 vs. *T. maritima* C277T in hard water (HW) (pH 10) at 20° C., 2.0 μg/mL heat-treated extract total soluble protein and 0 mg/mL liquid laundry detergent.

| Variant ID | SEQ ID NO: | Samples | Triacetin (mM) | $H_2O_2$[1] (mM) | Total soluble protein (μg/mL) | Liquid detergent (mg/mL) | Initial pH | PAA @ 5 min. (ppm) | PAA @ 20 min. (ppm) |
|---|---|---|---|---|---|---|---|---|---|
| | | no perhydrolase | 2 | 10 | 0 | 0 | 10 | 23 | 57 |
| Control | 5 | C277T | 2 | 10 | 2.0 | 0 | 10 | 64 | 121 |
| Control | 5 | C277T | 2 | 10 | 2.0 | 0 | 10 | 64 | 120 |
| 006E10 | 34 | R218C/C277T/F317L | 2 | 10 | 2.0 | 0 | 10 | 73 | 125 |
| 006E10 | 34 | R218C/C277T/F317L | 2 | 10 | 2.0 | 0 | 10 | 73 | 125 |
| 006A10 | 30 | F268S/C277T | 2 | 10 | 2.0 | 0 | 10 | 78 | 126 |
| 006A10 | 30 | F268S/C277T | 2 | 10 | 2.0 | 0 | 10 | 76 | 126 |

[1]= Hydrogen peroxide generated from sodium percarbonate.

EXAMPLE 9

Comparison of *Thermotoga maritime* Perhydrolase Variants Vs. *Thermotoga maritime* C277T Perhydrolase Under Simulated Laundry Care Application Conditions Two error-prone PCR (epPCR)-generated variant perhydrolases were assayed for peracetic acid (PAA) production under laundry application conditions (10 mL total volume, 1 mM triacetin (TA), 4.4 mM $H_2O_2$ from sodium percarbonate in hard water (HW, 400 ppm Ca ion), 1.0 μg/mL of heat-treated extract total soluble protein containing an error-prone PCR (epPCR)-generated variant perhydrolase prepared as described in Example 6) without added liquid laundry detergent and compared to PAA production using the same concentration of C277T variant perhydrolase (Published U.S. Patent Application No. 2010-0087529 to DiCosimo et al., SEQ ID NO: 5) (Table 9). Under these reaction conditions, variants 006G11 (D254G/C277T, SEQ ID NO: 46) and 006E12 (H227L/T233A/C277T/A290V, SEQ ID NO: 40) show a measurable improvement specific activity for peracetic acid production when compared to the C277T perhydrolase (SEQ ID NO: 5) from which the variants were prepared.

TABLE 9

Peracetic acid (PAA) production at 5 minutes and 20 minutes from variants 006G11 and 006E12 vs. *T. maritima* C277T in hard water (HW) (pH 9) at 20° C., 1.0 μg/mL heat-treated extract total soluble protein and 0 mg/mL liquid laundry detergent.

| Variant ID | SEQ ID NO: | Samples | Triacetin (mM) | $H_2O_2$[1] (mM) | Total soluble protein (μg/mL) | Liquid detergent (mg/mL) | Initial pH | PAA @ 5 min. (ppm) | PAA @ 20 min. (ppm) |
|---|---|---|---|---|---|---|---|---|---|
| | | no perhydrolase | 1 | 4.4 | 0 | 0 | 9 | 1.6 | 6.5 |
| Control | 5 | C277T | 1 | 4.4 | 1 | 0 | 9 | 9.0 | 26 |
| Control | 5 | C277T | 1 | 4.4 | 1 | 0 | 9 | 9.3 | 26 |

TABLE 9-continued

Peracetic acid (PAA) production at 5 minutes and 20 minutes from variants 006G11 and 006E12 vs. *T. maritima* C277T in hard water (HW) (pH 9) at 20° C., 1.0 μg/mL heat-treated extract total soluble protein and 0 mg/mL liquid laundry detergent.

| Variant ID | SEQ ID NO: | Samples | Triacetin (mM) | $H_2O_2$[1] (mM) | Total soluble protein (μg/mL) | Liquid detergent (mg/mL) | Initial pH | PAA @ 5 min. (ppm) | PAA @ 20 min. (ppm) |
|---|---|---|---|---|---|---|---|---|---|
| 006G11 | 46 | D254G/C277T | 1 | 4.4 | 1 | 0 | 9 | 13 | 33 |
| 006G11 | 46 | D254G/C277T | 1 | 4.4 | 1 | 0 | 9 | 13 | 32 |
| 006E12 | 40 | H227L/T233A/C277T/A290V | 1 | 4.4 | 1 | 0 | 9 | 12 | 31 |
| 006E12 | 40 | H227L/T233A/C277T/A290V | 1 | 4.4 | 1 | 0 | 9 | 12 | 31 |

[1]= Hydrogen peroxide generated from sodium percarbonate.

EXAMPLE 10

Comparison of Perhydrolase Variants Vs. *Thermotoga maritima* C277S Variant Perhydrolase Using 2 Mm 4-Acetoxybenzoic Acid and 10 Mm $H_2O_2$ in Sodium Bicarbonate Buffer (10 mM, pH 6.5) at 20° C.

Reactions (100 mL total volume) were run at 20° C. in sodium bicarbonate buffer (10 mM, pH 7.0) containing 4-acetoxybenzoic acid (4ABA, 2 mM), hydrogen peroxide (10 mM) and 2.0 μg/mL of heat-treated extract total soluble protein containing an error-prone PCR (epPCR)-generated variant perhydrolase prepared as described in Example 6. Reactions were stirred for only the first 45 seconds of reaction to initially mix the reactants and enzyme. A comparative reaction was also run under identical conditions to that described immediately above using 2.0 μg/mL of heat-treated extract total soluble protein isolated from *E. coli* KLP18/pSW228/C277S (expressing *Thermotoga maritime* C277S perhydrolase variant, SEQ ID NO: 69), where the heat-treated extract supernatant was prepared according to the procedure of Example 6, and where this heat-treated extract supernatant contained the same concentration of *Thermotoga maritime* C2775 perhydrolase variant (SEQ ID NO: 69) as a percentage of total soluble protein as was present in the heat-treated extract total soluble protein containing an error-prone PCR (epPCR)-generated variant perhydrolase. Variant 873B4 (A266P/C277S, SEQ ID NO: 102) showed a measurable improvement in specific activity for peracetic acid production at 5 min when compared to the C277S perhydrolase (SEQ ID NO: 69) from which the variant was prepared (Table 10).

TABLE 10

Peracetic acid (PAA) production at 5 minutes and 20 minutes from variants 873A4 and 873B4 vs. *T. maritima* C277S in sodium bicarbonate buffer (pH 7.0) at 20° C. with 2.0 μg/mL heat-treated extract total soluble protein.

| Variant ID | SEQ ID NO: | Samples | 4ABA (mM) | $H_2O_2$ (mM) | Total soluble protein (μg/mL) | Initial pH | PAA @ 5 min. (ppm) | PAA @ 20 min. (ppm) |
|---|---|---|---|---|---|---|---|---|
| | | no perhydrolase | 2 | 10 | 0 | 7.0 | 6 | 45 |
| Control | 69 | C277S | 2 | 10 | 2.0 | 7.0 | 15 | 48 |
| Control | 69 | C277S | 2 | 10 | 2.0 | 7.0 | 18 | 50 |
| 873A4 | 98 | L125M/C277S | 2 | 10 | 2.0 | 7.0 | 13 | 43 |
| 873A4 | 98 | L125M/C277S | 2 | 10 | 2.0 | 7.0 | 16 | 49 |
| 873B4 | 102 | A266P/C277S | 2 | 10 | 2.0 | 7.0 | 23 | 56 |
| 873B4 | 102 | A266P/C277S | 2 | 10 | 2.0 | 7.0 | 21 | 52 |

EXAMPLE 11

Comparison of a *Thermotoga maritime* Perhydrolase Variant vs. *Thermotoga maritima* C277T Perhydrolase Under Simulated Laundry Care Application Conditions An error-prone PCR (epPCR)-generated variant perhydrolase was evaluated for peracetic acid (PAA) production under laundry application conditions (10 mL total volume, 0.5 mM triacetin (TA), 2.0 mM $H_2O_2$ from sodium percarbonate at 25° C. in deionized water, 2.0 μg/mL of heat-treated extract total soluble protein containing an error-prone PCR (epPCR)-generated variant perhydrolase prepared as described in Example 6) using 2 g/L of solid laundry detergent (a formulation generally comprising surfactants (sodium dodecylbenzenesulfonate, C12-15 Pareth-5, C12-15 Pareth-7, sodium stearate, and stearic acid), builders (sodium carbonate, zeolite, sodium silicate, and citric acid), binders (cellulose, PEG-75, dextrin, and sucrose), bulking agents (sodium sulfate, sodium chloride, sodium bicarbonate, and calcium carbonate), structurants (sodium acrylic Acid/MA copolymer, and sodium polyacrylate), sequestrants (tetrasodium etidronate and calcium sodium EDTMP), optical brighteners (disodium anilinomorpholinotriazinylaminostilbenesulfonate), stabilizing agents, anti-redeposition agents, antifoaming agents, and softness extenders) and compared to PAA production using the same concentration of C277T variant perhydrolase (Published U.S. Patent Application No. 2010-0087529 to DiCosimo et al., SEQ ID NO: 5). The results of the various comparisons under simulated laundry care conditions are provided in Table 11. Under these reaction conditions, variant 006E10 (R218C/C277T/F317L, SEQ ID NO: 34) showed a measurable improvement in specific activity for peracetic acid production when compared to the *T. maritima* C277T perhydrolase (SEQ ID NO: 5) under the specified conditions (with added solid detergent at pH 10.7).

TABLE 11

Peracetic acid (PAA) production at 5 minutes and 20 minutes from variant 006E10 vs. *T. maritima* C277T in 2 mg/mL solid laundry detergent (pH 10.7) at 25° C., 2.0 μg/mL heat-treated extract total soluble protein.

| Variant ID | SEQ ID NO: | Samples | Triacetin (mM) | $H_2O_2$[1] (mM) | Total soluble protein (μg/mL) | Solid detergent (mg/mL) | Initial pH | PAA @ 5 min. (ppm) | PAA @ 10 min (ppm) | PAA @ 20 min. (ppm) |
|---|---|---|---|---|---|---|---|---|---|---|
| | | no perhydrolase | 0.5 | 2.0 | 0 | 2 | 10.7 | 2.2 | 4.3 | 5.6 |
| Control | 5 | C277T | 0.5 | 2.0 | 2.0 | 2 | 10.7 | 7.5 | 11 | 13 |
| 006E10 | 34 | R218C/C277T/F317L | 0.5 | 2.0 | 2.0 | 2 | 10.7 | 11 | 14 | 15 |

[1]= Hydrogen peroxide generated from sodium percarbonate.

What is claimed is:

1. An isolated polypeptide having perhydrolytic activity comprising the amino acid sequence of SEQ ID NO: 30.

2. The polypeptide of claim 1; wherein said polypeptide is characterized by a peracetic acid formation specific activity that is higher than the peracetic acid formation specific activity of the Thermotoga maritima C277T acetyl xylan esterase having amino acid sequence SEQ ID NO: 5.

3. A process for producing a peroxycarboxylic acid comprising:

(a) providing a set of reaction components comprising:

(1) at least one substrate selected from the group consisting of:

(i) one or more esters having the structure $[X]_mR_5$ wherein

X =an ester group of the formula $R_6$—C(O)O;

$R_6$ =C1 to C7 linear, branched or cyclic hydrocarbyl moiety, optionally substituted with hydroxyl groups or C1 to C4 alkoxy groups, wherein $R_6$ optionally comprises one or more ether linkages for $R_6$ =C2 to C7;

$R_5$ =a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m is an integer ranging from 1 to the number of carbon atoms in $R_5$; and wherein said esters have solubility in water of at least 5 ppm at 25° C.;

(ii) one or more glycerides having the structure

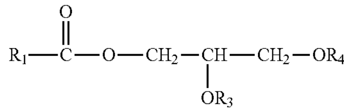

wherein $R_1$=C1 to C21 straight chain or branched chain alkyl optionally substituted with an hydroxyl or a C1 to C4 alkoxy group and $R_3$ and $R_4$ are individually H or $R_1$C(O);

(iii) one or more esters of the formula:

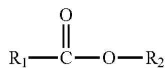

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10;

(iv) one or more acylated monosaccharides, acylated disaccharides, or acylated polysaccharides; and (v) any combination of (i) through (iv);

(2) a source of peroxygen; and (3) an enzyme catalyst comprising the polypeptide of claim 1;

(b) combining the set of reaction components under suitable reaction conditions whereby peroxycarboxylic acid is produced; and (c) optionally diluting the peroxycarboxylic acid produced in step (b).

4. The process of claim 3 further comprising the step of: d) contacting a hard surface or inanimate object with the peroxycarboxylic acid produced in step (b) or step (c); whereby said hard surface or said inanimate object is disinfected, bleached, destained or a combination thereof.

5. The process of claim 3 wherein the inanimate object is a medical instrument.

6. The process of claim 3 further comprising the step of: d) contacting an article of clothing or a textile with peroxycarboxylic acid produced in step (b) or step (c); whereby the article of clothing or textile receives a benefit.

7. The process of claim 6 wherein the benefit is selected from the group consisting of a disinfecting, sanitizing, bleaching, destaining, deodorizing, and combinations thereof.

8. The process of claim 3 further comprising the step of: d) contacting wood pulp or paper pulp with peroxycarboxylic acid produced in step (b) or step (c); whereby the wood pulp or paper pulp is bleached.

9. The process of claim 3 wherein the substrate is selected from the group consisting of: monoacetin; diacetin; triacetin; monopropionin; dipropionin;

tripropionin; monobutyrin; dibutyrin; tributyrin; glucose pentaacetate; β-D-galactose pentaacetate, sorbitol hexaacetate, sucrose octaacetate, xylose tetraacetate; acetylated xylan; acetylated xylan fragments; β-D-ribofuranose-1,2,3,5-tetraacetate; tri-O-acetyl-D-galactal; tri-O-acetyl-D-glucal; monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol; 4-acetoxybenzoic acid; and mixtures thereof.

10. The process of claim 9 wherein the substrate is triacetin.

11. The process of claim 3 wherein the peroxycarboxylic acid produced is peracetic acid, perpropionic acid, perbutyric acid, perlactic acid, perglycolic acid, permethoxyacetic acid, per-β-hydroxybutyric acid, or mixtures thereof.

12. The process of claim 3 wherein the enzyme catalyst is in the form of a microbial cell, a permeabilized microbial cell, a microbial cell extract, a partially purified enzyme, or a purified enzyme.

13. A composition comprising:

(a) a set of reaction components comprising:

(1) at least one substrate selected from the group consisting of:

(i) one or more esters having the structure $[X]_mR_5$ wherein

X =an ester group of the formula $R_6$-C(O)O;

$R_6$ =C1 to C7 linear, branched or cyclic hydrocarbyl moiety, optionally substituted with hydroxyl groups or C1 to C4 alkoxy groups, wherein $R_6$ optionally comprises one or more ether linkages for $R_6$ =C2 to C7;

$R_5$ =a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m is an integer ranging from 1 to the number of carbon atoms in $R_5$; and wherein said esters have solubility in water of at least 5 ppm at 25° C.;

(ii) one or more glycerides having the structure

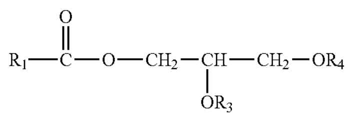

wherein $R_1$=C1 to C21 straight chain or branched chain alkyl optionally substituted with an hydroxyl or a C1 to C4 alkoxy group and $R_3$ and $R_4$ are individually H or $R_1C(O)$;

(iii) one or more esters of the formula:

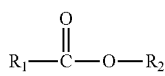

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10;

(iv) one or more acylated monosaccharides, acylated disaccharides, or acylated polysaccharides; and (v) any combination of (i) through (iv);

(2) a source of peroxygen; and (3) an enzyme catalyst comprising the polypeptide of claim 1; and (b) at least one peroxycarboxylic acid formed upon combining the set of reaction components of (a).

14. A peracid generation and delivery system comprising:

(a) a first compartment comprising (1) an enzyme catalyst comprising the polypeptide of claim 1;

(2) at least one substrate selected from the group consisting of:

(i) one or more esters having the structure $[X]_mR_5$ wherein

X =an ester group of the formula $R_6$-C(O)O;

$R_6$ =C1 to C7 linear, branched or cyclic hydrocarbyl moiety, optionally substituted with hydroxyl groups or C1 to C4 alkoxy groups, wherein $R_6$ optionally comprises one or more ether linkages for $R_6$ =C2 to C7;

$R_5$ =a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;

m is an integer ranging from 1 to the number of carbon atoms in $R_5$; and wherein said esters have solubility in water of at least 5 ppm at 25° C.;

(ii) one or more glycerides having the structure

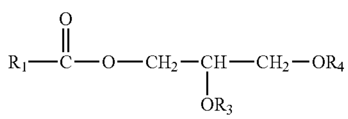

wherein $R_1$=C1 to C21 straight chain or branched chain alkyl optionally substituted with an hydroxyl or a C1 to C4 alkoxy group and $R_3$ and $R_4$ are individually H or $R_1C(O)$;

(iii) one or more esters of the formula:

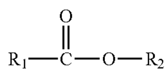

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10;

(iv) one or more acylated monosaccharides, acylated disaccharides, or acylated polysaccharides; and (v) any combination of (i) through (iv); and (3) an optional buffer; and (b) a second compartment comprising (1) source of peroxygen;

(2) a peroxide stabilizer; and (3) an optional buffer.

15. The peracid generation and delivery system of claim 14 wherein the substrate comprises triacetin.

16. A laundry care product comprising the polypeptide of claim 1.

17. A personal care product comprising the polypeptide of claim 1.

* * * * *

SEQUENCE LISTING

```
<160> NUMBER OF SEQ ID NOS: 116

<210> SEQ ID NO 1
<211> LENGTH: 978
<212> TYPE: DNA
<213> ORGANISM: Thermotoga maritima

<400> SEQUENCE: 1

atggccttct tcgatttacc actcgaagaa ctgaagaaat atcgtccaga gcggtacgaa      60

gagaaagact tcgatgagtt ctgggaagag acactcgcag agagcgaaaa gttcccctta     120

gaccccgtct tcgagaggat ggagtctcac ctcaaaacag tcgaagcgta cgatgtcacc     180

ttctccggat acaggggaca gaggatcaaa gggtggctcc ttgttccaaa actggaagaa     240

gaaaaacttc cctgcgttgt gcagtacata ggatacaacg gtggaagagg attccctcac     300

gactggctgt tctggccttc tatgggttac atatgtttcg tcatggatac tcgaggtcag     360

ggaagcggct ggctgaaagg agacacaccg gattaccctg agggtcccgt tgaccctcag     420

tatccaggat tcatgacaag aggaatactg gatcccagaa cttactacta cagacgagtc     480

ttcacggacg ctgtcagagc cgttgaagct gctgcttctt ttcctcaggt agatcaagaa     540

agaatcgtga tagctggagg cagtcagggt ggcggaatag cccttgcggt gagcgctctc     600

tcaaagaaag caaaggctct tctgtgcgat gtgccgtttc tgtgtcactt cagaagagca     660

gtacagcttg tggatacgca tccatacgcg gagatcacga actttctaaa gacccacaga     720

gacaaggaag aaatcgtgtt caggactctt tcctatttcg atggagtgaa cttcgcagcc     780

agagcgaaga tccctgcgct gtttttctgtg ggtctcatgg acaacatttg tcctccttca     840

acggttttcg ctgcctacaa ttactacgct ggaccgaagg aaatcagaat ctatccgtac     900

aacaaccacg agggaggagg ctctttccaa gcggttgaac aggtgaaatt cttgaaaaaa     960

ctatttgaga aaggctaa                                                   978

<210> SEQ ID NO 2
<211> LENGTH: 325
<212> TYPE: PRT
<213> ORGANISM: Thermotoga maritima

<400> SEQUENCE: 2

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
```

```
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Cys Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 3
<211> LENGTH: 23
<212> TYPE: DNA
<213> ORGANISM: artificial sequence
<220> FEATURE:
<223> OTHER INFORMATION: primer

<400> SEQUENCE: 3
tcggacaaca tcacctcctt cta 23

<210> SEQ ID NO 4
<211> LENGTH: 23
<212> TYPE: DNA
<213> ORGANISM: artificial sequence
<220> FEATURE:
<223> OTHER INFORMATION: primer

<400> SEQUENCE: 4

```
tagaaggagg tgagatgttg tcc                                               23

<210> SEQ ID NO 5
<211> LENGTH: 325
<212> TYPE: PRT
<213> ORGANISM: artificial sequence
<220> FEATURE:
<223> OTHER INFORMATION: synthetic construct

<400> SEQUENCE: 5

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 6
<211> LENGTH: 3674
<212> TYPE: DNA
```

```
<213> ORGANISM: artificial sequence
<220> FEATURE:
<223> OTHER INFORMATION: plasmid

<400> SEQUENCE: 6

gacgaaaggg cctcgtgata cgcctatttt tataggttaa tgtcatgata ataatggttt     60
cttagacgtc aggtggcact tttcggggaa atgtgcgcgg aacccctatt tgtttatttt    120
tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
```

```
accatgatta cgccaagctt gcatgcctgc agtaaggagg aataggacat ggcgttcttc   2280

gacctgcctc tggaagaact gaagaaatac cgtccagagc gttacgaaga gaaggacttc   2340

gacgagttct gggaggaaac tctggcggag agcgaaaagt ttccgctgga cccagtgttc   2400

gagcgtatgg aatctcacct gaaaaccgtg gaggcatatg acgttacttt ttctggttac   2460

cgtggccagc gtatcaaagg ctggctgctg gttccgaaac tggaggaaga aaaactgccg   2520

tgcgtagttc agtacatcgg ttacaacggt ggccgtggct ttccgcacga ttggctgttc   2580

tggccgtcta tgggctacat ttgcttcgtc atggatactc gtggtcaggg ttccggctgg   2640

ctgaaaggcg atactccgga ttatccggag ggcccggtag acccgcagta ccctggcttc   2700

atgacgcgtg gtattctgga tccgcgtacc tattactatc gccgcgtttt taccgatgca   2760

gttcgtgccg tagaggccgc ggcttctttc cctcaggttg accaggagcg tattgttatc   2820

gctggtggct cccagggtgg cggcatcgcc ctggcggtat ctgcgctgag caagaaagct   2880

aaggcactgc tgtgtgacgt cccgttcctg tgtcacttcc gtcgcgctgt tcagctggta   2940

gatacccatc cgtacgcgga gattactaac ttcctgaaaa ctcaccgcga caaagaagaa   3000

atcgttttcc gcaccctgtc ctatttcgac ggcgttaact tcgcggctcg tgcaaaaatt   3060

ccggcactgt tctctgttgg tctgatggac aacatcaccc ctccttctac cgttttcgcg   3120

gcatataact attatgcggg tccgaaagaa atccgtatct atccgtacaa caaccacgaa   3180

ggcggtggta gctttcaggc tgttgaacaa gtgaaattcc tgaagaaact gtttgagaag   3240

ggctaatcta gaggatcccc gggtaccgag ctcgaattca ctggccgtcg ttttacaacg   3300

tcgtgactgg gaaaaccctg gcgttaccca acttaatcgc cttgcagcac atcccccttt   3360

cgccagctgg cgtaatagcg aagaggcccg caccgatcgc ccttcccaac agttgcgcag   3420

cctgaatggc gaatggcgcc tgatgcggta ttttctcctt acgcatctgt gcggtatttc   3480

acaccgcata tggtgcactc tcagtacaat ctgctctgat gccgcatagt taagccagcc   3540

ccgacacccg ccaacacccg ctgacgcgcc ctgacgggct tgtctgctcc cggcatccgc   3600

ttacagacaa gctgtgaccg tctccgggag ctgcatgtgt cagaggtttt caccgtcatc   3660

accgaaacgc gcga                                                      3674


<210> SEQ ID NO 7
<211> LENGTH: 49
<212> TYPE: DNA
<213> ORGANISM: artificial sequence
<220> FEATURE:
<223> OTHER INFORMATION: primer

<400> SEQUENCE: 7

taactgcagt aaggaggaat aggacatggc gttcttcgac ctgcctctg                  49


<210> SEQ ID NO 8
<211> LENGTH: 38
<212> TYPE: DNA
<213> ORGANISM: artificial sequence
<220> FEATURE:
<223> OTHER INFORMATION: primer

<400> SEQUENCE: 8

tgatctagat tagcccttct caaacagttt ctttcagg                              38


<210> SEQ ID NO 9
<211> LENGTH: 978
<212> TYPE: DNA
<213> ORGANISM: artificial sequence
<220> FEATURE:
```

```
<223> OTHER INFORMATION: synthetic construct
<220> FEATURE:
<221> NAME/KEY: CDS
<222> LOCATION: (1)..(978)

<400> SEQUENCE: 9

atg gcg ttc ttc gac ctg cct ctg gaa gaa ctg aag aaa tac cgt cca      48
Met Ala Phe Phe Asp Leu Pro Leu Glu Glu Leu Lys Lys Tyr Arg Pro
1               5                   10                  15

gag cgt tac gaa gag aag gac ttc gac gag ttc agg gag gaa act ctg      96
Glu Arg Tyr Glu Glu Lys Asp Phe Asp Glu Phe Arg Glu Glu Thr Leu
            20                  25                  30

gcg gag agc gaa aag ttt ccg ctg gac cca gtg ttc gag cgt atg gaa     144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac     192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa     240
Arg Gly Gln Arg Ile Lys Gly Trp Leu Leu Val Pro Lys Leu Glu Glu
65                  70                  75                  80

gaa aaa ctg tcg tgc gta gtt cag tac atc ggt tac aac ggt ggc cgt     288
Glu Lys Leu Ser Cys Val Val Gln Tyr Ile Gly Tyr Asn Gly Gly Arg
                85                  90                  95

ggc ttt ccg cac gat tgg ctg ttc tgg ccg tct atg ggc tac att tgc     336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat     384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc     432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt     480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag     528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc     576
Val Asp Gln Glu Arg Ile Val Ile Ala Gly Gly Ser Gln Gly Gly Gly
            180                 185                 190

atc gcc ctg gcg gta tct gcg ctg ggc aag aaa gct aag gca ctg ctg     624
Ile Ala Leu Ala Val Ser Ala Leu Gly Lys Lys Ala Lys Ala Leu Leu
        195                 200                 205

tgt gac gtc ccg ttc ctg tgt cac ttc cgt cgc gct gtt cag ctg gta     672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc     720
Asp Thr His Pro Tyr Ala Glu Ile Thr Asn Phe Leu Lys Thr His Arg
225                 230                 235                 240

gac aaa gat gaa atc gtt ttc cgc acc ctg tcc tat ttc gac ggc gtt     768
Asp Lys Asp Glu Ile Val Phe Arg Thr Leu Ser Tyr Phe Asp Gly Val
                245                 250                 255

aac ttc gcg gct cgt gca aaa att ccg gca ctg ttc tct gtt ggt ctg     816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat     864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa     912
```

```
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 10
<211> LENGTH: 325
<212> TYPE: PRT
<213> ORGANISM: artificial sequence
<220> FEATURE:
<223> OTHER INFORMATION: Synthetic Construct

<400> SEQUENCE: 10

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Arg Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Ser Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Gly Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Asp Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320
```

```
Leu Phe Glu Lys Gly
                325


<210> SEQ ID NO 11
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 11

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255
```

```
aac ttc gcg gct agt gca aaa ttt ccg gca ctg ttc tct gtt ggt ctg      816
Asn Phe Ala Ala Ser Ala Lys Phe Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325
```

```
<210> SEQ ID NO 12
<211> LENGTH: 325
<212> TYPE: PRT
<213> ORGANISM: artificial sequence
<220> FEATURE:
<223> OTHER INFORMATION: Synthetic Construct

<400> SEQUENCE: 12

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Ser Ala Lys Phe Pro Ala Leu Phe Ser Val Gly Leu
```

```
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 13
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 13

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgt gag gaa act ccg       96
Glu Arg Tyr Glu Glu Lys Asp Phe Asp Glu Phe Cys Glu Glu Thr Pro
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gaa ccg cgt acc tat tac tat cgc cgc gtt      480
Met Thr Arg Gly Ile Leu Glu Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
```

```
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 14
<211> LENGTH: 325
<212> TYPE: PRT
<213> ORGANISM: artificial sequence
<220> FEATURE:
<223> OTHER INFORMATION: Synthetic Construct

<400> SEQUENCE: 14

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Cys Glu Glu Thr Pro
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Glu Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205
```

```
Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 15
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 15

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgt gag gaa act ctg       96
Glu Arg Tyr Glu Glu Lys Asp Phe Asp Glu Phe Cys Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg tcc tgg ccg tct atg ggc tac att tgc      336
Gly Phe Pro His Asp Trp Leu Ser Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175
```

```
gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 16
<211> LENGTH: 325
<212> TYPE: PRT
<213> ORGANISM: artificial sequence
<220> FEATURE:
<223> OTHER INFORMATION: Synthetic Construct

<400> SEQUENCE: 16

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Cys Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Ser Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160
```

```
Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 17
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 17

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
```

```
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gat atc gct ggt ggc tcc cag ggt ggc ggc      576
Val Asp Gln Glu Arg Ile Asp Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 18
<211> LENGTH: 325
<212> TYPE: PRT
<213> ORGANISM: artificial sequence
<220> FEATURE:
<223> OTHER INFORMATION: Synthetic Construct

<400> SEQUENCE: 18

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
```

```
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Asp Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 19
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 19

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95
```

```
ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ccg aag aaa      960
Gly Gly Gly Ser Phe Gln Ala Val Glu Gln Val Lys Phe Pro Lys Lys
305                 310                 315                 320

ctg ttt gag aag ggc taa                                              978
Leu Phe Glu Lys Gly
                325
```

<210> SEQ ID NO 20
<211> LENGTH: 325
<212> TYPE: PRT
<213> ORGANISM: artificial sequence
<220> FEATURE:
<223> OTHER INFORMATION: Synthetic Construct

<400> SEQUENCE: 20

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45
```

```
Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Pro Lys Lys
305                 310                 315                 320

Leu Phe Glu Lys Gly
                325


<210> SEQ ID NO 21
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 21

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
```

```
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ctg gca ctg ttc tct gtt ggt ctg      816
Asn Phe Ala Ala Arg Ala Lys Ile Leu Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt aac tat ccg tac aac aac cac gaa      912
Tyr Ala Gly Pro Lys Glu Ile Arg Asn Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 22
<211> LENGTH: 325
<212> TYPE: PRT
<213> ORGANISM: artificial sequence
<220> FEATURE:
<223> OTHER INFORMATION: Synthetic Construct

<400> SEQUENCE: 22
```

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Leu Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Asn Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 23
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 23

```
atg gcg ttc ttc gac ctg cct ctg gaa gaa ctg aag aaa tac cgt cta       48
Met Ala Phe Phe Asp Leu Pro Leu Glu Glu Leu Lys Lys Tyr Arg Leu
1               5                   10                  15
```

```
gag cgt tac gaa gag aag gac ttc gac gag ttc tgg gag gaa act ctg        96
Glu Arg Tyr Glu Glu Lys Asp Phe Asp Glu Phe Trp Glu Glu Thr Leu
            20                  25                  30

gcg gag agc gaa aag ttc ccg ctg gac cca gtg ttc gag cgt atg gaa       144
Ala Glu Ser Glu Lys Phe Pro Leu Asp Pro Val Phe Glu Arg Met Glu
        35                  40                  45

tct cac ctg aaa aac gtg gag gca tat gac gtt act ttt tct ggt tac       192
Ser His Leu Lys Asn Val Glu Ala Tyr Asp Val Thr Phe Ser Gly Tyr
    50                  55                  60

cgt ggc cag cgt atc aaa ggc tgg ctg ctg gtt ccg aaa ctg gag gaa       240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt       288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc       336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat       384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc       432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc tgc gtt       480
Met Thr Arg Gly Ile Leu Asp Pro Arg Thr Tyr Tyr Tyr Arg Cys Val
145                 150                 155                 160

ttt acc gat gca gtt cgt gcc gta gag gcc gcg gct tct ttc cct cag       528
Phe Thr Asp Ala Val Arg Ala Val Glu Ala Ala Ala Ser Phe Pro Gln
                165                 170                 175

gtt gac cag gag cgt att gat atc gct ggt ggc tcc cag ggt ggc ggc       576
Val Asp Gln Glu Arg Ile Asp Ile Ala Gly Gly Ser Gln Gly Gly Gly
            180                 185                 190

atc gcc ctg gcg gta tct gcg ctg agc aag aaa gct aag gca ctg ctg       624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta       672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc       720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt       768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg       816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat       864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa       912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa       960
Gly Gly Gly Ser Phe Gln Ala Val Glu Gln Val Lys Phe Leu Lys Lys
305                 310                 315                 320

ctg ttt gag aag ggc taa                                               978
Leu Phe Glu Lys Gly
                325
```

```
<210> SEQ ID NO 24
<211> LENGTH: 325
<212> TYPE: PRT
<213> ORGANISM: artificial sequence
<220> FEATURE:
<223> OTHER INFORMATION: Synthetic Construct

<400> SEQUENCE: 24

Met Ala Phe Phe Asp Leu Pro Leu Glu Glu Leu Lys Lys Tyr Arg Leu
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Asn Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Cys Val
145                 150                 155                 160

Phe Thr Asp Ala Val Arg Ala Val Glu Ala Ala Ala Ser Phe Pro Gln
                165                 170                 175

Val Asp Gln Glu Arg Ile Asp Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 25
<211> LENGTH: 978
<212> TYPE: DNA
<213> ORGANISM: artificial sequence
<220> FEATURE:
```

```
<223> OTHER INFORMATION: synthetic construct
<220> FEATURE:
<221> NAME/KEY: CDS
<222> LOCATION: (1)..(978)

<400> SEQUENCE: 25

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cat      528
Phe Thr Asp Ala Val Arg Ala Val Glu Ala Ala Ala Ser Phe Pro His
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg cag      624
Ile Ala Leu Ala Val Ser Ala Leu Ser Lys Lys Ala Lys Ala Leu Gln
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
```

```
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 26
<211> LENGTH: 325
<212> TYPE: PRT
<213> ORGANISM: artificial sequence
<220> FEATURE:
<223> OTHER INFORMATION: Synthetic Construct

<400> SEQUENCE: 26

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro His
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Gln
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320
```

```
Leu Phe Glu Lys Gly
                325


<210> SEQ ID NO 27
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 27

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ccg       96
Glu Arg Tyr Glu Glu Lys Asp Phe Asp Glu Phe Trp Glu Glu Thr Pro
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255
```

```
aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 28
<211> LENGTH: 325
<212> TYPE: PRT
<213> ORGANISM: artificial sequence
<220> FEATURE:
<223> OTHER INFORMATION: Synthetic Construct

<400> SEQUENCE: 28

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Pro
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
```

```
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 29
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 29

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
```

```
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg tcc tct gtt ggt ctg      816
Asn Phe Ala Ala Arg Ala Lys Ile Pro Ala Leu Ser Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 30
<211> LENGTH: 325
<212> TYPE: PRT
<213> ORGANISM: artificial sequence
<220> FEATURE:
<223> OTHER INFORMATION: Synthetic Construct

<400> SEQUENCE: 30

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205
```

```
Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Ser Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 31
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 31

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg ggg gaa act ctg       96
Glu Arg Tyr Glu Glu Lys Asp Phe Asp Glu Phe Trp Gly Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt cct ggt tac      192
Ser His Leu Lys Thr Val Glu Ala Tyr Asp Val Thr Phe Pro Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct tta cct cag      528
Phe Thr Asp Ala Val Arg Ala Val Glu Ala Ala Ala Ser Leu Pro Gln
                165                 170                 175
```

```
gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 32
<211> LENGTH: 325
<212> TYPE: PRT
<213> ORGANISM: artificial sequence
<220> FEATURE:
<223> OTHER INFORMATION: Synthetic Construct

<400> SEQUENCE: 32

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Gly Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Pro Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160
```

```
Phe Thr Asp Ala Val Arg Ala Val Glu Ala Ala Ala Ser Leu Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 33
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 33

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
```

```
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc tgt cgc gct gtt cag ctg gta      672
Cys Asp Val Pro Phe Leu Cys His Phe Cys Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ctc ctg aag aaa      960
Gly Gly Gly Ser Phe Gln Ala Val Glu Gln Val Lys Leu Leu Lys Lys
305                 310                 315                 320

ctg ttt gag aag ggc taa                                              978
Leu Phe Glu Lys Gly
                325


<210> SEQ ID NO 34
<211> LENGTH: 325
<212> TYPE: PRT
<213> ORGANISM: artificial sequence
<220> FEATURE:
<223> OTHER INFORMATION: Synthetic Construct

<400> SEQUENCE: 34

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
```

```
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Cys Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Leu Leu Lys Lys
305                 310                 315                 320

Leu Phe Glu Lys Gly
                325


<210> SEQ ID NO 35
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 35

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95
```

```
ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cct atc tat ccg tac aac aac cac gaa      912
Tyr Ala Gly Pro Lys Glu Ile Pro Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325
```

```
<210> SEQ ID NO 36
<211> LENGTH: 325
<212> TYPE: PRT
<213> ORGANISM: artificial sequence
<220> FEATURE:
<223> OTHER INFORMATION: Synthetic Construct

<400> SEQUENCE: 36

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45
```

```
Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Pro Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 37
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 37

```
atg gcg ttc ttc gac ctg cct ctg aaa gaa ctg aag aaa tac cgt cca       48
Met Ala Phe Phe Asp Leu Pro Leu Lys Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
```

```
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac tgc gtt      768
Asp Lys Glu Glu Ile Val Phe Arg Thr Leu Ser Tyr Phe Asp Cys Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325
```

<210> SEQ ID NO 38
<211> LENGTH: 325
<212> TYPE: PRT
<213> ORGANISM: artificial sequence
<220> FEATURE:
<223> OTHER INFORMATION: Synthetic Construct

<400> SEQUENCE: 38

```
Met Ala Phe Phe Asp Leu Pro Leu Lys Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Cys Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 39
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 39

```
atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15
```

```
gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cta ccg tac gcg gag att gct aac ttc ctg aaa act cac cgc      720
Asp Thr Leu Pro Tyr Ala Glu Ile Ala Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gtg ggt ccg aaa gaa atc cgt atc tat ccg tac aac aac cac gaa      912
Tyr Val Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325
```

<210> SEQ ID NO 40
<211> LENGTH: 325
<212> TYPE: PRT
<213> ORGANISM: artificial sequence
<220> FEATURE:
<223> OTHER INFORMATION: Synthetic Construct

<400> SEQUENCE: 40

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr Leu Pro Tyr Ala Glu Ile Ala Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Val Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 41
<211> LENGTH: 978
<212> TYPE: DNA
<213> ORGANISM: artificial sequence
<220> FEATURE:

```
<223> OTHER INFORMATION: synthetic construct
<220> FEATURE:
<221> NAME/KEY: CDS
<222> LOCATION: (1)..(978)

<400> SEQUENCE: 41

atg gcg ttc ttc gac ctg cct ctg gaa gaa ctg aag aaa tac cgt cca      48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg      96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa     144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac     192
Ser His Leu Lys Thr Val Glu Ala Tyr Asp Val Thr Phe Ser Gly Tyr
    50                  55                  60

cgt ggc cgg cgt atc aaa ggc tgg ctg ctg gtt ccg aaa ctg gag gaa     240
Arg Gly Arg Arg Ile Lys Gly Trp Leu Leu Val Pro Lys Leu Glu Glu
65                  70                  75                  80

gaa gaa ctg ccg tgc gta gtt cag tac atc ggt tac aac ggt ggc cgt     288
Glu Glu Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc     336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat     384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc     432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt     480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag     528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc     576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg     624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta     672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc     720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt     768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg     816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat     864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa     912
```

```
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 42
<211> LENGTH: 325
<212> TYPE: PRT
<213> ORGANISM: artificial sequence
<220> FEATURE:
<223> OTHER INFORMATION: Synthetic Construct

<400> SEQUENCE: 42

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Arg Arg Ile Lys Gly Trp Leu Leu Val Pro Lys Leu Glu Glu
65                  70                  75                  80

Glu Glu Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320
```

```
Leu Phe Glu Lys Gly
                325


<210> SEQ ID NO 43
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 43

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ctc cgc acc ctg tcc tat ttc gac ggc gtt      768
Asp Lys Glu Glu Ile Val Leu Arg Thr Leu Ser Tyr Phe Asp Gly Val
                245                 250                 255
```

```
aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gat ttc gcg gca tat aac tat      864
Met Asp Asn Ile Thr Pro Pro Ser Thr Asp Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 44
<211> LENGTH: 325
<212> TYPE: PRT
<213> ORGANISM: artificial sequence
<220> FEATURE:
<223> OTHER INFORMATION: Synthetic Construct

<400> SEQUENCE: 44

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Leu Arg Thr Leu Ser Tyr Phe Asp Gly Val
                245                 250                 255

Asn Phe Ala Ala Arg Ala Lys Ile Pro Ala Leu Phe Ser Val Gly Leu
```

```
            260                 265                 270

Met Asp Asn Ile Thr Pro Pro Ser Thr Asp Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 45
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 45

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
```

```
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc ggc ggc gtt      768
Asp Lys Glu Glu Ile Val Phe Arg Thr Leu Ser Tyr Phe Gly Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325
```

<210> SEQ ID NO 46
<211> LENGTH: 325
<212> TYPE: PRT
<213> ORGANISM: artificial sequence
<220> FEATURE:
<223> OTHER INFORMATION: Synthetic Construct

<400> SEQUENCE: 46

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205
```

```
Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Gly Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 47
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 47

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gtg cgt tac gaa gag aag gac ttc gac gag ttc tgg gag gaa act ctg       96
Val Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175
```

```
gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cat gca aaa att ccg gca ctg ttc tct gtt ggt ctg      816
Asn Phe Ala Ala His Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 48
<211> LENGTH: 325
<212> TYPE: PRT
<213> ORGANISM: artificial sequence
<220> FEATURE:
<223> OTHER INFORMATION: Synthetic Construct

<400> SEQUENCE: 48

Met Ala Phe Phe Asp Leu Pro Leu Glu Glu Leu Lys Lys Tyr Arg Pro
1               5                   10                  15

Val Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160
```

```
Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala His Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 49
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 49

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ctc gac gag ttc tgg gag gaa tct ctg       96
Glu Arg Tyr Glu Glu Lys Asp Leu Asp Glu Phe Trp Glu Glu Ser Leu
            20                  25                  30

gcg gag agc gaa aag ttt ccg ctg gac cca gtg ttc gag cgt atg gta      144
Ala Glu Ser Glu Lys Phe Pro Leu Asp Pro Val Phe Glu Arg Met Val
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
```

```
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg gaa ttc ctg aag aaa      960
Gly Gly Gly Ser Phe Gln Ala Val Glu Gln Val Glu Phe Leu Lys Lys
305                 310                 315                 320

ctg ttt gag aag ggc taa                                              978
Leu Phe Glu Lys Gly
                325


<210> SEQ ID NO 50
<211> LENGTH: 325
<212> TYPE: PRT
<213> ORGANISM: artificial sequence
<220> FEATURE:
<223> OTHER INFORMATION: Synthetic Construct

<400> SEQUENCE: 50

Met Ala Phe Phe Asp Leu Pro Leu Glu Glu Leu Lys Lys Tyr Arg Pro
1               5                   10                  15

Glu Arg Tyr Glu Glu Lys Asp Leu Asp Glu Phe Trp Glu Glu Ser Leu
            20                  25                  30

Ala Glu Ser Glu Lys Phe Pro Leu Asp Pro Val Phe Glu Arg Met Val
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
```

```
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Glu Phe Leu Lys Lys
305                 310                 315                 320

Leu Phe Glu Lys Gly
                325


<210> SEQ ID NO 51
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 51

atg gcg ttc ttc gac ctg cct ctg gaa gaa ctg aag aaa tac cgt cca      48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg      96
Glu Arg Tyr Glu Glu Lys Asp Phe Asp Glu Phe Trp Glu Glu Thr Leu
            20                  25                  30

gcg gag agc gaa aag ttt ccg ctg gac cca ggg ttc gag cgt atg gaa     144
Ala Glu Ser Glu Lys Phe Pro Leu Asp Pro Gly Phe Glu Arg Met Glu
        35                  40                  45

tct cac ctg aaa acc gtg gag gca tat gac gtt act ttt tct tgt tac     192
Ser His Leu Lys Thr Val Glu Ala Tyr Asp Val Thr Phe Ser Cys Tyr
    50                  55                  60

cgt ggc cag cgt atc aaa ggc tgg ctg ctg gtt ccg aaa ctg gag gaa     240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt     288
Glu Lys Leu Pro Cys Val Val Gln Tyr Ile Gly Tyr Asn Gly Gly Arg
                85                  90                  95
```

```
ggc ttt ccg ctc gat tgg ctg ttc tgg ccg tct atg ggc tac att tgc      336
Gly Phe Pro Leu Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gtg gca tat aac tat      864
Met Asp Asn Ile Thr Pro Pro Ser Thr Val Phe Val Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325
```

<210> SEQ ID NO 52
<211> LENGTH: 325
<212> TYPE: PRT
<213> ORGANISM: artificial sequence
<220> FEATURE:
<223> OTHER INFORMATION: Synthetic Construct

<400> SEQUENCE: 52

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Gly Phe Glu Arg Met Glu
        35                  40                  45
```

```
Ser His Leu Lys Thr Val Glu Ala Tyr Asp Val Thr Phe Ser Cys Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro Leu Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Val Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 53
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 53

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
```

```
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac tac gcg gct cgt gca aaa att ccg gca ctg ttc tct gtt ggt ctg      816
Asn Tyr Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gga atc cgt atc tat ccg tac aac aac cac gaa      912
Tyr Ala Gly Pro Lys Gly Ile Arg Ile Tyr Pro Tyr Asn Asn His Glu
    290                 295                 300

ggc ggt ggt agc ttt cag gct gtt gaa caa gtg aaa ttc ccg aag aaa      960
Gly Gly Gly Ser Phe Gln Ala Val Glu Gln Val Lys Phe Pro Lys Lys
305                 310                 315                 320

ctg ttt gag aag ggc taa                                              978
Leu Phe Glu Lys Gly
                325
```

<210> SEQ ID NO 54
<211> LENGTH: 325
<212> TYPE: PRT
<213> ORGANISM: artificial sequence
<220> FEATURE:
<223> OTHER INFORMATION: Synthetic Construct

<400> SEQUENCE: 54

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Tyr Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Gly Ile Arg Ile Tyr Pro Tyr Asn Asn His Glu
    290                 295                 300

Gly Gly Gly Ser Phe Gln Ala Val Glu Gln Val Lys Phe Pro Lys Lys
305                 310                 315                 320

Leu Phe Glu Lys Gly
                325
```

<210> SEQ ID NO 55
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 55

```
atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15
```

```
gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

tta acc gat gca gtt cgt gcc gta gag gcc gcg gct tct ttc cct cag      528
Leu Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325
```

<210> SEQ ID NO 56
<211> LENGTH: 325
<212> TYPE: PRT
<213> ORGANISM: artificial sequence
<220> FEATURE:
<223> OTHER INFORMATION: Synthetic Construct

<400> SEQUENCE: 56

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Leu Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 57
<211> LENGTH: 978
<212> TYPE: DNA
<213> ORGANISM: artificial sequence
<220> FEATURE:

```
<223> OTHER INFORMATION: synthetic construct
<220> FEATURE:
<221> NAME/KEY: CDS
<222> LOCATION: (1)..(978)

<400> SEQUENCE: 57

atg gcg ttc ttc gac ctg cct ctg gaa gaa ctg aag aaa tac cgt cca      48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg      96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa     144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac     192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa     240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt     288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc     336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat     384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc     432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt     480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag     528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc     576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg     624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta     672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc     720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat tcc gac ggc gtt     768
Asp Lys Glu Glu Ile Val Phe Arg Thr Leu Ser Tyr Ser Asp Gly Val
                245                 250                 255

aac ttc gcg gct cgt gca aaa att ccg gca ctg ttc tct gtt ggt ctg     816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat     864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa     912
```

```
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 58
<211> LENGTH: 325
<212> TYPE: PRT
<213> ORGANISM: artificial sequence
<220> FEATURE:
<223> OTHER INFORMATION: Synthetic Construct

<400> SEQUENCE: 58

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Ser Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320
```

```
Leu Phe Glu Lys Gly
                325


<210> SEQ ID NO 59
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 59

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac atc gac gag ttc tgg gag gaa act ctg       96
Glu Arg Tyr Glu Glu Lys Asp Ile Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255
```

```
aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325
```

<210> SEQ ID NO 60
<211> LENGTH: 325
<212> TYPE: PRT
<213> ORGANISM: artificial sequence
<220> FEATURE:
<223> OTHER INFORMATION: Synthetic Construct

<400> SEQUENCE: 60

```
Met Ala Phe Phe Asp Leu Pro Leu Glu Glu Leu Lys Lys Tyr Arg Pro
1               5                   10                  15

Glu Arg Tyr Glu Glu Lys Asp Ile Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
```

```
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 61
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 61

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag aca ctg ctg      624
Ile Ala Leu Ala Val Ser Ala Leu Ser Lys Lys Ala Lys Thr Leu Leu
        195                 200                 205

tgt gac gtc ccg ttc ctg tgt cac ttc cgt cgc gct gtt cag ctg gta      672
```

```
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 62
<211> LENGTH: 325
<212> TYPE: PRT
<213> ORGANISM: artificial sequence
<220> FEATURE:
<223> OTHER INFORMATION: Synthetic Construct

<400> SEQUENCE: 62

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Thr Leu Leu
        195                 200                 205
```

```
Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 63
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 63

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg aag gca tat gac gtt act ttt tct ggt tac      192
Ser His Leu Lys Thr Val Lys Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175
```

```
gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 64
<211> LENGTH: 325
<212> TYPE: PRT
<213> ORGANISM: artificial sequence
<220> FEATURE:
<223> OTHER INFORMATION: Synthetic Construct

<400> SEQUENCE: 64

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Lys Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160
```

```
Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 65
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 65

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cgg cgt atc aaa ggc tgg ctg ctg gtt ccg aaa ctg gag gaa      240
Arg Gly Arg Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
```

```
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc acc cct cct tct acc gtt ttc gcg gca tat aac tat      864
Met Asp Asn Ile Thr Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 66
<211> LENGTH: 325
<212> TYPE: PRT
<213> ORGANISM: artificial sequence
<220> FEATURE:
<223> OTHER INFORMATION: Synthetic Construct

<400> SEQUENCE: 66

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Arg Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
```

```
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 67
<211> LENGTH: 23
<212> TYPE: DNA
<213> ORGANISM: artificial sequence
<220> FEATURE:
<223> OTHER INFORMATION: synthetic construct

<400> SEQUENCE: 67

ggacaacatc tcacctcctt cta                                              23


<210> SEQ ID NO 68
<211> LENGTH: 23
<212> TYPE: DNA
<213> ORGANISM: artificial sequence
<220> FEATURE:
<223> OTHER INFORMATION: synthetic construct

<400> SEQUENCE: 68

tagaaggagg tgagatgttg tcc                                              23


<210> SEQ ID NO 69
<211> LENGTH: 325
<212> TYPE: PRT
<213> ORGANISM: artificial sequence
<220> FEATURE:
<223> OTHER INFORMATION: synthetic construct

<400> SEQUENCE: 69

Met Ala Phe Phe Asp Leu Pro Leu Glu Glu Leu Lys Lys Tyr Arg Pro
1               5                   10                  15
```

```
Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 70
<211> LENGTH: 3674
<212> TYPE: DNA
<213> ORGANISM: artificial sequence
<220> FEATURE:
<223> OTHER INFORMATION: synthetic construct

<400> SEQUENCE: 70

```
gacgaaaggg cctcgtgata cgcctatttt tataggttaa tgtcatgata ataatggttt     60

cttagacgtc aggtggcact tttcggggaa atgtgcgcgg aacccctatt tgtttatttt    120

tctaaataca ttcaaatatg tatccgctca tgagacaata accctgataa atgcttcaat    180

aatattgaaa aaggaagagt atgagtattc aacatttccg tgtcgccctt attccctttt    240

ttgcggcatt ttgccttcct gtttttgctc acccagaaac gctggtgaaa gtaaaagatg    300
```

```
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt gcatgcctgc agtaaggagg aataggacat ggcgttcttc   2280
gacctgcctc tggaagaact gaagaaatac cgtccagagc gttacgaaga gaaggacttc   2340
gacgagttct gggaggaaac tctggcggag agcgaaaagt ttccgctgga cccagtgttc   2400
gagcgtatgg aatctcacct gaaaaccgtg gaggcatatg acgttacttt ttctggttac   2460
cgtggccagc gtatcaaagg ctggctgctg gttccgaaac tggaggaaga aaaactgccg   2520
tgcgtagttc agtacatcgg ttacaacggt ggccgtggct ttccgcacga ttggctgttc   2580
tggccgtcta tgggctacat ttgcttcgtc atggatactc gtggtcaggg ttccggctgg   2640
ctgaaaggcg atactccgga ttatccggag ggcccggtag acccgcagta ccctggcttc   2700
```

```
atgacgcgtg gtattctgga tccgcgtacc tattactatc gccgcgtttt taccgatgca   2760

gttcgtgccg tagaggccgc ggcttctttc cctcaggttg accaggagcg tattgttatc   2820

gctggtggct cccagggtgg cggcatcgcc ctggcggtat ctgcgctgag caagaaagct   2880

aaggcactgc tgtgtgacgt cccgttcctg tgtcacttcc gtcgcgctgt tcagctggta   2940

gatacccatc cgtacgcgga gattactaac ttcctgaaaa ctcaccgcga caaagaagaa   3000

atcgttttcc gcaccctgtc ctatttcgac ggcgttaact tcgcggctcg tgcaaaaatt   3060

ccggcactgt tctctgttgg tctgatggac aacatcagcc ctccttctac cgttttcgcg   3120

gcatataact attatgcggg tccgaaagaa atccgtatct atccgtacaa caaccacgaa   3180

ggcggtggta gctttcaggc tgttgaacaa gtgaaattcc tgaagaaact gtttgagaag   3240

ggctaatcta gaggatcccc gggtaccgag ctcgaattca ctggccgtcg ttttacaacg   3300

tcgtgactgg gaaaaccctg gcgttaccca acttaatcgc cttgcagcac atcccccttt   3360

cgccagctgg cgtaatagcg aagaggcccg caccgatcgc ccttcccaac agttgcgcag   3420

cctgaatggc gaatggcgcc tgatgcggta ttttctcctt acgcatctgt gcggtatttc   3480

acaccgcata tggtgcactc tcagtacaat ctgctctgat gccgcatagt taagccagcc   3540

ccgacacccg ccaacacccg ctgacgcgcc ctgacgggct tgtctgctcc cggcatccgc   3600

ttacagacaa gctgtgaccg tctccgggag ctgcatgtgt cagaggtttt caccgtcatc   3660

accgaaacgc gcga                                                     3674
```

```
<210> SEQ ID NO 71
<211> LENGTH: 41
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (20)..(22)
<223> OTHER INFORMATION: n is a, c, g, or t

<400> SEQUENCE: 71

ggaggaaact ctggcggagn nngaaaagtt tccgctggac c                         41


<210> SEQ ID NO 72
<211> LENGTH: 41
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (20)..(22)
<223> OTHER INFORMATION: n is a, c, g, or t

<400> SEQUENCE: 72

ggtccagcgg aaacttttcn nnctccgcca gagtttcctc c                         41


<210> SEQ ID NO 73
<211> LENGTH: 39
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (18)..(20)
<223> OTHER INFORMATION: n is a, c, g, or t

<400> SEQUENCE: 73
```

gctggctgct ggttccgnnn ctggaggaag aaaaactgc 39

<210> SEQ ID NO 74
<211> LENGTH: 39
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (20)..(22)
<223> OTHER INFORMATION: n is a, c, g, or t

<400> SEQUENCE: 74
gcagtttttc ttcctccagn nncggaacca gcagccagc 39

<210> SEQ ID NO 75
<211> LENGTH: 37
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (19)..(21)
<223> OTHER INFORMATION: n is a, c, g, or t

<400> SEQUENCE: 75
ggtcagggtt ccggctggnn naaaggcgat actccgg 37

<210> SEQ ID NO 76
<211> LENGTH: 37
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (17)..(19)
<223> OTHER INFORMATION: n is a, c, g, or t

<400> SEQUENCE: 76
ccggagtatc gcctttnnnc cagccggaac cctgacc 37

<210> SEQ ID NO 77
<211> LENGTH: 43
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (19)..(21)
<223> OTHER INFORMATION: n is a, c, g, or t

<400> SEQUENCE: 77
gctcgtgcaa aaattccgnn nctgttctct gttggtctga tgg 43

<210> SEQ ID NO 78
<211> LENGTH: 43
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (23)..(25)
<223> OTHER INFORMATION: n is a, c, g, or t

<400> SEQUENCE: 78
ccatcagacc aacagagaac agnnncggaa tttttgcacg agc 43

<210> SEQ ID NO 79
<211> LENGTH: 40
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (20)..(22)
<223> OTHER INFORMATION: n is a, c, g, or t

<400> SEQUENCE: 79
ctctgttggt ctgatggacn nnatcagccc tccttctacc 40

<210> SEQ ID NO 80
<211> LENGTH: 40
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (19)..(21)
<223> OTHER INFORMATION: n is a, c, g, or t

<400> SEQUENCE: 80
ggtagaagga gggctgatnn ngtccatcag accaacagag 40

<210> SEQ ID NO 81
<211> LENGTH: 39
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (19)..(21)
<223> OTHER INFORMATION: n is a, c, g, or t

<400> SEQUENCE: 81
cgtatctatc cgtacaacnn ncacgaaggc ggtggtagc 39

<210> SEQ ID NO 82
<211> LENGTH: 39
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (19)..(21)
<223> OTHER INFORMATION: n is a, c, g, or t

<400> SEQUENCE: 82
gctaccaccg ccttcgtgnn ngttgtacgg atagatacg 39

<210> SEQ ID NO 83
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 83

```
atg gcg ttc ttc gac ctg cct ctg gaa gaa ctg aag aaa tac cgt cca      48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg      96
Glu Arg Tyr Glu Glu Lys Asp Phe Asp Glu Phe Trp Glu Glu Thr Leu
            20                  25                  30

gcg gag cgc gaa aag ttt ccg ctg gac cca gtg ttc gag cgt atg gaa     144
Ala Glu Arg Glu Lys Phe Pro Leu Asp Pro Val Phe Glu Arg Met Glu
        35                  40                  45

tct cac ctg aaa acc gtg gag gca tat gac gtt act ttt tct ggt tac     192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa     240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt     288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc     336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat     384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc     432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt     480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag     528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc     576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg     624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta     672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc     720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt     768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg     816
Asn Phe Ala Ala Arg Ala Lys Ile Pro Ala Leu Phe Ser Val Gly Leu
            260                 265                 270

atg gac aac atc agc cct cct tct acc gtt ttc gcg gca tat aac tat     864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa     912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa     960
Gly Gly Gly Ser Phe Gln Ala Val Glu Gln Val Lys Phe Leu Lys Lys
305                 310                 315                 320
```

```
ctg ttt gag aag ggc taa                                              978
Leu Phe Glu Lys Gly
                325


<210> SEQ ID NO 84
<211> LENGTH: 325
<212> TYPE: PRT
<213> ORGANISM: artificial sequence
<220> FEATURE:
<223> OTHER INFORMATION: Synthetic Construct

<400> SEQUENCE: 84

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Arg Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 85
<211> LENGTH: 978
```

```
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 85

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag aaa gaa aag ttt ccg ctg gac cca gtg ttc gag cgt atg gaa      144
Ala Glu Lys Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
```

```
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 86
<211> LENGTH: 325
<212> TYPE: PRT
<213> ORGANISM: artificial sequence
<220> FEATURE:
<223> OTHER INFORMATION: Synthetic Construct

<400> SEQUENCE: 86

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Lys Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300
```

```
Gly Gly Gly Ser Phe Gln Ala Val Glu Gln Val Lys Phe Leu Lys Lys
305                 310                 315                 320

Leu Phe Glu Lys Gly
                325


<210> SEQ ID NO 87
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 87

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag gaa gaa aag ttt ccg ctg gac cca gtg ttc gag cgt atg gaa      144
Ala Glu Glu Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240
```

```
gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 88
<211> LENGTH: 325
<212> TYPE: PRT
<213> ORGANISM: artificial sequence
<220> FEATURE:
<223> OTHER INFORMATION: Synthetic Construct

<400> SEQUENCE: 88

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Glu Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
```

```
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 89
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 89

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag aac gaa aag ttt ccg ctg gac cca gtg ttc gag cgt atg gaa      144
Ala Glu Asn Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
```

```
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 90
<211> LENGTH: 325
<212> TYPE: PRT
<213> ORGANISM: artificial sequence
<220> FEATURE:
<223> OTHER INFORMATION: Synthetic Construct

<400> SEQUENCE: 90

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Asn Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190
```

```
Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 91
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 91

atg gcg ttc ttc gac ctg cct ctg gaa gaa ctg aag aaa tac cgt cca      48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg      96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa     144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac     192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg gcg ctg gag gaa     240
Arg Gly Gln Arg Ile Lys Gly Trp Leu Leu Val Pro Ala Leu Glu Glu
65                  70                  75                  80

gaa aaa ctg ccg tgc gta gtt cag tac atc ggt tac aac ggt ggc cgt     288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc     336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat     384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc     432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt     480
Met Thr Arg Gly Ile Leu Asp Pro Arg Thr Tyr Tyr Tyr Arg Arg Val
145                 150                 155                 160
```

```
ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 92
<211> LENGTH: 325
<212> TYPE: PRT
<213> ORGANISM: artificial sequence
<220> FEATURE:
<223> OTHER INFORMATION: Synthetic Construct

<400> SEQUENCE: 92

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Ala Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140
```

```
Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 93
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 93

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg gtg ctg gag gaa      240
Arg Gly Gln Arg Ile Lys Gly Trp Leu Leu Val Pro Val Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
```

```
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 94
<211> LENGTH: 325
<212> TYPE: PRT
<213> ORGANISM: artificial sequence
<220> FEATURE:
<223> OTHER INFORMATION: Synthetic Construct

<400> SEQUENCE: 94

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Val Leu Glu Glu
65                  70                  75                  80

Glu Lys Leu Pro Cys Val Val Gln Tyr Ile Gly Tyr Asn Gly Gly Arg
```

```
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 95
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 95

atg gcg ttc ttc gac ctg cct ctg gaa gaa ctg aag aaa tac cgt cca        48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg        96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa       144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac       192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg gac ctg gag gaa       240
Arg Gly Gln Arg Ile Lys Gly Trp Leu Leu Val Pro Asp Leu Glu Glu
65                  70                  75                  80
```

```
gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325
```

<210> SEQ ID NO 96
<211> LENGTH: 325
<212> TYPE: PRT
<213> ORGANISM: artificial sequence
<220> FEATURE:
<223> OTHER INFORMATION: Synthetic Construct

<400> SEQUENCE: 96

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30
```

```
Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Asp Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 97
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 97

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
```

```
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg atg aaa ggc gat      384
Phe Val Met Asp Thr Arg Gly Gln Gly Ser Gly Trp Met Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg      816
Asn Phe Ala Ala Arg Ala Lys Ile Pro Ala Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325
```

<210> SEQ ID NO 98
<211> LENGTH: 325
<212> TYPE: PRT
<213> ORGANISM: artificial sequence
<220> FEATURE:

```
<223> OTHER INFORMATION: Synthetic Construct

<400> SEQUENCE: 98

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 99
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 99
```

```
atg gcg ttc ttc gac ctg cct ctg gaa gaa ctg aag aaa tac cgt cca      48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg      96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa     144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac     192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa     240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt     288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc     336
Gly Phe Pro His Asp Trp Leu Phe Trp Pro Ser Met Gly Tyr Ile Cys
            100                 105                 110

ttc gtc atg gat act cgt ggt cag ggt tcc ggc tgg cgc aaa ggc gat     384
Phe Val Met Asp Thr Arg Gly Gln Gly Ser Gly Trp Arg Lys Gly Asp
        115                 120                 125

act ccg gat tat ccg gag ggc ccg gta gac ccg cag tac cct ggc ttc     432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt     480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag     528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc     576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg     624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta     672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc     720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt     768
Asp Lys Glu Glu Ile Val Phe Arg Thr Leu Ser Tyr Phe Asp Gly Val
                245                 250                 255

aac ttc gcg gct cgt gca aaa att ccg gca ctg ttc tct gtt ggt ctg     816
Asn Phe Ala Ala Arg Ala Lys Ile Pro Ala Leu Phe Ser Val Gly Leu
            260                 265                 270

atg gac aac atc agc cct cct tct acc gtt ttc gcg gca tat aac tat     864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa     912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa     960
Gly Gly Gly Ser Phe Gln Ala Val Glu Gln Val Lys Phe Leu Lys Lys
305                 310                 315                 320
```

```
ctg ttt gag aag ggc taa                                           978
Leu Phe Glu Lys Gly
                325
```

<210> SEQ ID NO 100
<211> LENGTH: 325
<212> TYPE: PRT
<213> ORGANISM: artificial sequence
<220> FEATURE:
<223> OTHER INFORMATION: Synthetic Construct

<400> SEQUENCE: 100

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Arg Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 101
<211> LENGTH: 978

```
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 101

atg gcg ttc ttc gac ctg cct ctg gaa gaa ctg aag aaa tac cgt cca      48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg      96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa     144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac     192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa     240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt     288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc     336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat     384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc     432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt     480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag     528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc     576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg     624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta     672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc     720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt     768
Asp Lys Glu Glu Ile Val Phe Arg Thr Leu Ser Tyr Phe Asp Gly Val
                245                 250                 255

aac ttc gcg gct cgt gca aaa att ccg cca ctg ttc tct gtt ggt ctg     816
Asn Phe Ala Ala Arg Ala Lys Ile Pro Pro Leu Phe Ser Val Gly Leu
            260                 265                 270

atg gac aac atc agc cct cct tct acc gtt ttc gcg gca tat aac tat     864
Met Asp Asn Ile Ser Pro Pro Ser Thr Val Phe Ala Ala Tyr Asn Tyr
```

```
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 102
<211> LENGTH: 325
<212> TYPE: PRT
<213> ORGANISM: artificial sequence
<220> FEATURE:
<223> OTHER INFORMATION: Synthetic Construct

<400> SEQUENCE: 102

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Pro Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300
```

```
Gly Gly Gly Ser Phe Gln Ala Val Glu Gln Val Lys Phe Leu Lys Lys
305                 310                 315                 320

Leu Phe Glu Lys Gly
                325


<210> SEQ ID NO 103
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 103

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240
```

```
gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gac ctg ttc tct gtt ggt ctg      816
Asn Phe Ala Ala Arg Ala Lys Ile Pro Asp Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 104
<211> LENGTH: 325
<212> TYPE: PRT
<213> ORGANISM: artificial sequence
<220> FEATURE:
<223> OTHER INFORMATION: Synthetic Construct

<400> SEQUENCE: 104

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
```

```
                245                 250                 255

Asn Phe Ala Ala Arg Ala Lys Ile Pro Asp Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 105
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 105

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
```

```
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg ata ctg ttc tct gtt ggt ctg      816
Asn Phe Ala Ala Arg Ala Lys Ile Pro Ile Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 106
<211> LENGTH: 325
<212> TYPE: PRT
<213> ORGANISM: artificial sequence
<220> FEATURE:
<223> OTHER INFORMATION: Synthetic Construct

<400> SEQUENCE: 106

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190
```

```
Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ile Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 107
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 107

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160
```

```
ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg gag ctg ttc tct gtt ggt ctg      816
Asn Phe Ala Ala Arg Ala Lys Ile Pro Glu Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 108
<211> LENGTH: 325
<212> TYPE: PRT
<213> ORGANISM: artificial sequence
<220> FEATURE:
<223> OTHER INFORMATION: Synthetic Construct

<400> SEQUENCE: 108

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140
```

```
Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Glu Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 109
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 109

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
```

```
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg aac ctg ttc tct gtt ggt ctg      816
Asn Phe Ala Ala Arg Ala Lys Ile Pro Asn Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 110
<211> LENGTH: 325
<212> TYPE: PRT
<213> ORGANISM: artificial sequence
<220> FEATURE:
<223> OTHER INFORMATION: Synthetic Construct

<400> SEQUENCE: 110

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
```

```
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Asn Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 111
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 111

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80
```

```
gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg agg ctg ttc tct gtt ggt ctg      816
Asn Phe Ala Ala Arg Ala Lys Ile Pro Arg Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325


<210> SEQ ID NO 112
<211> LENGTH: 325
<212> TYPE: PRT
<213> ORGANISM: artificial sequence
<220> FEATURE:
<223> OTHER INFORMATION: Synthetic Construct

<400> SEQUENCE: 112

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30
```

```
Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Arg Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325


<210> SEQ ID NO 113
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 113

atg gcg ttc ttc gac ctg cct ctg gaa gaa ctg aag aaa tac cgt cca       48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg       96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa      144
Ala Glu Ser Glu Lys Phe Pro Leu Asp Pro Val Phe Glu Arg Met Glu
```

```
        35                  40                  45

tct cac ctg aaa acc gtg gag gca tat gac gtt act ttt tct ggt tac      192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa      240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt      288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc      336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat      384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc      432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt      480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag      528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc      576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg      624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta      672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc      720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt      768
Asp Lys Glu Glu Ile Val Phe Arg Thr Leu Ser Tyr Phe Asp Gly Val
                245                 250                 255

aac ttc gcg gct cgt gca aaa att ccg caa ctg ttc tct gtt ggt ctg      816
Asn Phe Ala Ala Arg Ala Lys Ile Pro Gln Leu Phe Ser Val Gly Leu
            260                 265                 270

atg gac aac atc agc cct cct tct acc gtt ttc gcg gca tat aac tat      864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa      912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa      960
Gly Gly Gly Ser Phe Gln Ala Val Glu Gln Val Lys Phe Leu Lys Lys
305                 310                 315                 320

ctg ttt gag aag ggc taa                                              978
Leu Phe Glu Lys Gly
                325
```

```
<210> SEQ ID NO 114
<211> LENGTH: 325
<212> TYPE: PRT
<213> ORGANISM: artificial sequence
<220> FEATURE:
```

<223> OTHER INFORMATION: Synthetic Construct

<400> SEQUENCE: 114

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Gln Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 115
<211> LENGTH: 978
<212> TYPE: DNA
<213> ORGANISM: artificial sequence
<220> FEATURE:
<223> OTHER INFORMATION: synthetic construct
<220> FEATURE:
<221> NAME/KEY: CDS
<222> LOCATION: (1)..(978)

<400> SEQUENCE: 115

```
atg gcg ttc ttc gac ctg cct ctg gaa gaa ctg aag aaa tac cgt cca        48
Met Ala Phe Phe Asp Leu Pro Leu Glu Glu Leu Lys Lys Tyr Arg Pro
1               5                   10                  15

gag cgt tac gaa gag aag gac ttc gac gag ttc tgg gag gaa act ctg        96
Glu Arg Tyr Glu Glu Lys Asp Phe Asp Glu Phe Trp Glu Glu Thr Leu
            20                  25                  30

gcg gag agc gaa aag ttt ccg ctg gac cca gtg ttc gag cgt atg gaa       144
Ala Glu Ser Glu Lys Phe Pro Leu Asp Pro Val Phe Glu Arg Met Glu
        35                  40                  45

tct cac ctg aaa acc gtg gag gca tat gac gtt act ttt tct ggt tac       192
Ser His Leu Lys Thr Val Glu Ala Tyr Asp Val Thr Phe Ser Gly Tyr
    50                  55                  60

cgt ggc cag cgt atc aaa ggc tgg ctg ctg gtt ccg aaa ctg gag gaa       240
Arg Gly Gln Arg Ile Lys Gly Trp Leu Leu Val Pro Lys Leu Glu Glu
65                  70                  75                  80

gaa aaa ctg ccg tgc gta gtt cag tac atc ggt tac aac ggt ggc cgt       288
Glu Lys Leu Pro Cys Val Val Gln Tyr Ile Gly Tyr Asn Gly Gly Arg
                85                  90                  95

ggc ttt ccg cac gat tgg ctg ttc tgg ccg tct atg ggc tac att tgc       336
Gly Phe Pro His Asp Trp Leu Phe Trp Pro Ser Met Gly Tyr Ile Cys
            100                 105                 110

ttc gtc atg gat act cgt ggt cag ggt tcc ggc tgg ctg aaa ggc gat       384
Phe Val Met Asp Thr Arg Gly Gln Gly Ser Gly Trp Leu Lys Gly Asp
        115                 120                 125

act ccg gat tat ccg gag ggc ccg gta gac ccg cag tac cct ggc ttc       432
Thr Pro Asp Tyr Pro Glu Gly Pro Val Asp Pro Gln Tyr Pro Gly Phe
    130                 135                 140

atg acg cgt ggt att ctg gat ccg cgt acc tat tac tat cgc cgc gtt       480
Met Thr Arg Gly Ile Leu Asp Pro Arg Thr Tyr Tyr Tyr Arg Arg Val
145                 150                 155                 160

ttt acc gat gca gtt cgt gcc gta gag gcc gcg gct tct ttc cct cag       528
Phe Thr Asp Ala Val Arg Ala Val Glu Ala Ala Ala Ser Phe Pro Gln
                165                 170                 175

gtt gac cag gag cgt att gtt atc gct ggt ggc tcc cag ggt ggc ggc       576
Val Asp Gln Glu Arg Ile Val Ile Ala Gly Gly Ser Gln Gly Gly Gly
            180                 185                 190

atc gcc ctg gcg gta tct gcg ctg agc aag aaa gct aag gca ctg ctg       624
Ile Ala Leu Ala Val Ser Ala Leu Ser Lys Lys Ala Lys Ala Leu Leu
        195                 200                 205

tgt gac gtc ccg ttc ctg tgt cac ttc cgt cgc gct gtt cag ctg gta       672
Cys Asp Val Pro Phe Leu Cys His Phe Arg Arg Ala Val Gln Leu Val
    210                 215                 220

gat acc cat ccg tac gcg gag att act aac ttc ctg aaa act cac cgc       720
Asp Thr His Pro Tyr Ala Glu Ile Thr Asn Phe Leu Lys Thr His Arg
225                 230                 235                 240

gac aaa gaa gaa atc gtt ttc cgc acc ctg tcc tat ttc gac ggc gtt       768
Asp Lys Glu Glu Ile Val Phe Arg Thr Leu Ser Tyr Phe Asp Gly Val
                245                 250                 255

aac ttc gcg gct cgt gca aaa att ccg gtg ctg ttc tct gtt ggt ctg       816
Asn Phe Ala Ala Arg Ala Lys Ile Pro Val Leu Phe Ser Val Gly Leu
            260                 265                 270

atg gac aac atc agc cct cct tct acc gtt ttc gcg gca tat aac tat       864
Met Asp Asn Ile Ser Pro Pro Ser Thr Val Phe Ala Ala Tyr Asn Tyr
        275                 280                 285

tat gcg ggt ccg aaa gaa atc cgt atc tat ccg tac aac aac cac gaa       912
Tyr Ala Gly Pro Lys Glu Ile Arg Ile Tyr Pro Tyr Asn Asn His Glu
    290                 295                 300

ggc ggt ggt agc ttt cag gct gtt gaa caa gtg aaa ttc ctg aag aaa       960
Gly Gly Gly Ser Phe Gln Ala Val Glu Gln Val Lys Phe Leu Lys Lys
305                 310                 315                 320
```

```
ctg ttt gag aag ggc taa                                               978
Leu Phe Glu Lys Gly
                325


<210> SEQ ID NO 116
<211> LENGTH: 325
<212> TYPE: PRT
<213> ORGANISM: artificial sequence
<220> FEATURE:
<223> OTHER INFORMATION: Synthetic Construct

<400> SEQUENCE: 116

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Val Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```